US012751715B2

(12) United States Patent
Levy et al.

(10) Patent No.: US 12,751,715 B2
(45) Date of Patent: Oct. 6, 2026

(54) SURGICAL DEVICES FOR BONE

(71) Applicant: Expand Medical Ltd., Amirim (IL)

(72) Inventors: Arie Levy, Shoam (IL); Ofek Levin, Amirim (IL)

(73) Assignee: Expand Medical Ltd., Amirim (IL)

(*) Notice: Subject to any disclaimer, the term of this patent is extended or adjusted under 35 U.S.C. 154(b) by 222 days.

(21) Appl. No.: 18/653,341

(22) Filed: May 2, 2024

(65) Prior Publication Data

US 2024/0366218 A1 Nov. 7, 2024

Related U.S. Application Data

(60) Provisional application No. 63/463,794, filed on May 3, 2023.

(51) Int. Cl.

| | |
|---|---|
| ***A61B 17/064*** | (2006.01) |
| ***A61B 17/00*** | (2006.01) |
| ***A61B 17/04*** | (2006.01) |
| ***A61B 17/072*** | (2006.01) |
| ***A61B 17/10*** | (2006.01) |
| ***A61B 17/16*** | (2006.01) |
| ***A61B 17/56*** | (2006.01) |

(Continued)

(52) U.S. Cl.

CPC .......... *A61B 17/0642* (2013.01); *A61B 17/10* (2013.01); *A61B 17/1604* (2013.01); *A61B 2017/00668* (2013.01); *A61B 17/0401* (2013.01); *A61B 2017/0409* (2013.01); *A61B 2017/0647* (2013.01); *A61B 17/07207* (2013.01); *A61B 17/1613* (2013.01); *A61B 2017/564* (2013.01); *A61B 17/846* (2013.01); *A61F 2/0811* (2013.01); *A61F 2002/0817* (2013.01); *A61F 2002/0829* (2013.01); *A61F 2002/0847* (2013.01); *A61F 2002/0888* (2013.01); *A61F 2220/0016* (2013.01)

(58) Field of Classification Search

CPC ............ A61B 17/0642; A61B 17/0401; A61B 17/064; A61B 17/10; A61B 17/1604; A61B 17/846; A61B 17/92; A61B 17/068; A61B 17/07207; A61B 17/16; A61B 17/1613; A61B 2017/564; A61B 2017/0647; A61B 2017/0409; A61B 2017/00668; A61F 2/0811; A61F 2002/0888; A61F 2002/0817; A61F 2002/0829; A61F 2002/0847; A61F 2220/0016

USPC ... 606/75, 300, 310, 329, 331, 86 R, 96–99, 606/104, 916

See application file for complete search history.

(56) References Cited

U.S. PATENT DOCUMENTS 4,627,437 A 12/1986 Bedi et al.
5,681,333 A 10/1997 Burkhart et al.

(Continued)

FOREIGN PATENT DOCUMENTS

WO 2022/056102 A1 3/2022
WO 2022/178080 A1 8/2022

*Primary Examiner* — Marcela I. Shirsat

(74) *Attorney, Agent, or Firm* — Zachary D. Hyde; Sullivan & Worcester LLP

(57) ABSTRACT

The disclosure provides systems, methods, and devices for making attachments to bone. Bone anchor systems use tools that have elongated shafts useful in arthroscopic or keyhole surgeries. In the bone anchor system, a tool is taken to the site once and used to both make the hole into the bone or tissue and simultaneously carry the anchor into the hole that is being made.

19 Claims, 19 Drawing Sheets

(51) Int. Cl.

| | |
|---|---|
| ***A61B 17/84*** | (2006.01) |
| ***A61F 2/08*** | (2006.01) |

(56) References Cited

U.S. PATENT DOCUMENTS

| | | | |
|---|---|---|---|
| 5,899,939 | A | 5/1999 | Boyce et al. |
| 6,235,058 | B1 | 5/2001 | Huene |
| 6,387,041 | B1 | 5/2002 | Harari et al. |
| 6,514,274 | B1 | 2/2003 | Boucher et al. |
| 6,652,561 | B1 | 11/2003 | Tran |
| 7,491,217 | B1 | 2/2009 | Hendren et al. |
| 8,277,458 | B2 | 10/2012 | Schneider |
| 8,298,285 | B2 | 10/2012 | Sklar et al. |
| 8,414,613 | B2 | 4/2013 | Huxel et al. |
| 8,778,023 | B2 | 7/2014 | Sklar |
| 8,915,961 | B2 | 12/2014 | Sungun et al. |
| 9,125,650 | B2 | 9/2015 | Euteneuer et al. |
| 9,289,202 | B2 | 3/2016 | Martin |
| 9,370,356 | B2 | 6/2016 | Euteneuer et al. |
| 9,439,753 | B2 | 9/2016 | Bouduban et al. |
| 9,770,534 | B2 | 9/2017 | Montes De Oca Balderas et al. |
| 9,888,952 | B2 | 2/2018 | Drapeau et al. |
| 10,085,736 | B2 | 10/2018 | McCarty, III |
| 10,568,627 | B2 | 2/2020 | Guo et al. |
| 10,806,444 | B2 | 10/2020 | Reeser et al. |
| 10,912,640 | B2 | 2/2021 | Euteneuer et al. |
| 11,006,949 | B2 | 5/2021 | Daniel |
| 11,076,851 | B2 | 8/2021 | Westling et al. |
| 11,123,058 | B2 | 9/2021 | Hernandez |
| 11,413,032 | B2 | 8/2022 | Running et al. |
| 2002/0050277 | A1 | 5/2002 | Beyar |
| 2003/0139752 | A1 | 7/2003 | Pasricha et al. |
| 2004/0087981 | A1 | 5/2004 | Berube et al. |
| 2005/0251143 | A1 | 11/2005 | Dillard |
| 2008/0051796 | A1 | 2/2008 | Nycz et al. |
| 2010/0082046 | A1 | 4/2010 | Harris et al. |
| 2012/0203340 | A1 | 8/2012 | Choinski et al. |
| 2012/0245631 | A1 | 9/2012 | Lunn et al. |
| 2013/0153628 | A1 | 6/2013 | Euteneuer |
| 2016/0113643 | A1 | 4/2016 | Diduch et al. |
| 2018/0235746 | A1 | 8/2018 | Pilgeram et al. |
| 2019/0167254 | A1 | 6/2019 | Balboa et al. |
| 2021/0275290 | A1* | 9/2021 | Domecus .............. A61F 2/0811 |

* cited by examiner

SURGICAL DEVICES FOR BONE

TECHNICAL FIELD

The disclosure relates to surgical devices.

BACKGROUND OF THE INVENTION

Injury or damage to joints in the body can be painful. Common causes of such injury include intense activity and age-related tissue deterioration. For example, ligament tears may arise from degenerative changes that occur with aging or from acute injuries during sports or other intensive activity. Treating those injuries to the musculoskeletal system is what defines the medical specialties of orthopedics and orthopedic surgery. Common orthopedic surgeries include repairs of the spine, shoulder, hand, hip, or knee, among others. For example, some people may suffer from a painful shoulder injury in the form a tear to one of a group tendons in the shoulder known as the rotator cuff. A complete tear of a rotator cuff tendon can be very painful and cause the loss of arm function. Orthopedic surgeries address those injuries. Orthopedic surgery is not without drawbacks. For example, the practical reality of surgical conditions in so-called keyhole or arthroscopic surgery means there is limited access to the surgical site.

SUMMARY OF THE INVENTION

The disclosure provides systems, methods, and devices for making attachments bone. Devices of the disclosure are particularly useful in orthopedic surgery and particular for keyhole or arthroscopic surgeries such as for joint repair, e.g., rotator cuff repair. Using device of disclosure, a graft (or ligament, suture, tendon, etc.) may be attached to a bone. With a graft positioned on bone, a system of the invention includes a delivery tool and a bone anchor carried on the delivery tool. The tool has a blade that extends through and beyond the anchor.

The blade is preferably rigid and sharp, and the blade pierces a hole through a graft and into bone (preferred embodiments have two parallel blades carrying a flat, spade-like anchor between them). The blade(s) of the delivery tip pierce the hole into the bone and carry the anchor into the hole. The blade(s) are then retracted, leaving the stake of the anchor driven into the bone. The anchor has a wide head that works like a cap to hold down the graft onto the bone.

Preferably, the delivery tool has a pair of bladed than extend from a rod that extends from a handle and through a shaft of the device. The bone anchor is carried between the two blades. A surgeon can navigate the shaft through a surgical incision or cannula and position the anchor at a target sit over bone (and over a graft positioned on the bone). The surgeon can drive the blades (and the carried anchor) into the bone, which may be accomplished by tapping a base of the handle with a mallet. The handle also includes a mechanism to retract the blades into the handle. The mechanism preferably include a threaded fitting around a base of the rod wherein a knob exposed at the handle can be turned to withdraw the blades into the handle via a screw drive provided by the threaded fitting. A distal end of the shaft has a bridge, tab, or overhang that sits behind the base of the anchor. As the surgeon screws the knob, the bridge, tab, or overhang keeps the anchor sitting in the bone while the blades are withdrawn slowly and gently into the shaft (leaving only the anchor in the bone).

The bone anchor system uses tools that have elongated shafts extending from handles. Those shafts are designed for ease of insertion through a minimally invasive surgical incision or trocar, such as those made and used in arthroscopic or keyhole surgeries. Thus these anchoring system are useful during joint repair, to bring anchors into the surgical site and anchor a graft to bone (e.g., using the bone anchor system). In each case, the tool is taken to the site once and used to both make the hole into the bone or tissue and simultaneously carry the anchor into the hole that is being made. Using systems of the invention, the surgeon does not need to make pilot holes or cuts first, and then return with a separate tool to place the anchor or attachment device. This avoids problems with misalignment and risky do-overs. Also, the attachment devices of the disclosure provide secure, durable attachment.

In certain aspects, the disclosure provides a bone anchor delivery system. The system includes a delivery tool comprising a handle, an elongated shaft extending from the handle, and a first blade extending distally from the shaft to a sharpened bone-piercing tip. The system also includes an implantable bone anchor disposed upon the blade. The bone anchor includes a base, a stake extending substantially perpendicular from the base, and an open portion in the base through which the first blade extends. Preferably the stake is substantially flat, comprising first and second opposed substantially planar surfaces; first and second barbed or serrated edges where the first and second surface meet; and a distal point. A flat side of the first blade (of the delivery tool) may lie against the first substantially planar surface of the stake of the bone anchor. The open portion in the base of the implantable anchor may define a substantially oval hole through the base in which a flat side of the oval hole cooperates with the first substantially planar surface of the stake to define an essentially flat surface against which the first blade lies.

The shaft of the delivery tool may include a slidable rod operable to translate the first blade between a first, distal position (in which the first blade extends distally from the shaft) and a second, proximal position (in which the blade is retracted proximally into the handle).

In some embodiments, the delivery tool includes an insertion sleeve disposed slidably over the shaft. A distal end of the insertion sleeve may be opened by sliding the insertion sleeve in a proximal direction over the elongated shaft. The delivery tool further may have a slider knob on the handle such that pushing the slider knob and sliding the slider knob in a proximal direction slides the insertion sleeve in the proximal direction over the elongated shaft. Preferably, the insertion sleeve comprises an elastic deformable material and a has slit separating two portions of a distal tip of the insertion sleeve. The insertion sleeve opens by bending the two portions of the distal tip elastically away from one another. In preferred embodiments, retracting the insertion sleeve exposes the bone anchor and/or blade in a distal direction out of the protection sleeve.

In certain embodiments, the bone anchor comprises at least one sloped face providing a transition between a flat surface of the stake and a proximal-most face of the base. The sloped face—when a sharpened tip of the first blade is positioned within a cutaway space defined by the sloped face—guides the bone anchor into position while the bone anchor is being loaded onto the delivery tool. The bone anchor may include first and second sloped faces, one at an outer perimeter of the base and another at the perimeter of the opening through the base. The opening through base may have a trapezoidal shape or other beveled or geometrical shape, to mimic a cross-sectional shape of the first sharp blade, providing rotation resistance and better fitment when the bone anchor is carried on the first sharp blade.

In preferred embodiments, the delivery tool comprises a second blade, and the first and second blade sit against respective opposed surfaces of the stake of the bone anchor. The second blade is preferably slidable through the shaft independently of the first blade. In some embodiments, when the first blade and the second blade are in distal positions with the stake of the bone anchor therebetween, the first blade, the second blade, and the stake cooperate to present a sharpened tapered tip useful to pierce into bone.

A proximal end of the handle may present a flat or solid head surface. In some embodiments, when the sharpened tapered tip is positioned against bone and the flat or solid head surface is hammered with a mallet, the sharpened tapered tip pierces a hole in the bone and the delivery tool carries the bone anchor into the bone down to the base.

Preferably the first and second blades are independently slidable away from the sharpened tapered tip in a proximal direction into the elongated shaft to leave the implantable bone anchor uncoupled from the delivery tool and anchored into bone.

In some embodiments, the first and second blades comprise a rigid material such as a metal, the bone anchor comprises a pliable polymer, and the first and second blades prevent the bone anchor from deforming during delivery. Preferably the stake of the bone anchor has a plurality of teeth along first and second edges. The base of the bone anchor may overhang and extend away from the stake in multiple directions. When the bone anchor is passed through a graft or ligament and into bone, the overhangs hold the graft or ligament against the bone.

In related aspects, the disclosure provides a method of anchoring a graft or ligament to bone. The method involves using a bone anchor delivery system as described above. The implantable bone anchor has a stake that is sandwiched between two blades extending from the elongated shaft of the delivery tool. When the first blade and the second blade are in distal positions with the stake of the bone anchor therebetween, first blade, the second blade, and the stake cooperate to present a sharpened tapered tip useful to pierce into bone.

A surgeon navigates the elongated shaft to a surgical site. For example, the surgeon may insert the shaft through a cannula or incision during arthroscopic or keyhole surgery. The sharped tip (with the blades and the anchors) is positioned at a target. For example, the surgery may include a graft or ligament positioned over bone, where the surgeon intends to attach the graft or ligament to the bone. Using the delivery tool, the sharpened tip is inserted through any graft or ligament and into the bone. For example, the surgeon may tap a base of the handle with a mallet to effectively hammer the implantable bone anchor into the bone.

The first and second blades (e.g., preferably sharpened metal) puncture the surface of the bone and create a hole into the bone, while carrying the implantable anchor between them. The anchor is driven to depth, i.e., to the point at which it bottoms out so that the base holds the graft or ligament onto the bone. Notably, at least one of the blades passes through a hole in the base. Preferably the shaft has a bridge that holds the anchor in the bone during the retracting step. The retracting step includes screwing a knob on a handle to draw the blade into the handle without any kinetic shocks or reciprocal motions on the delivery tool. The blades make a thin rectangular hole in the bone and toothed or serrated edges of the stake of the anchor have a wider extent than a width of the blades.

The blades only displace material or leave voids along an axis that is not same as an axis along which barbs or serrations of the bone anchor spread. That is, the bone anchor has barbed or serrated edges that extend laterally and define an attachment axis. The blades do not compromise any bone material along that axis and do not leave any voids in the bone beyond the barbed or serrated edges along the attachment axis.

The teeth or serrations provide good purchase into the bone and the implantable anchor does not fall out. At least one of the blades had been extended through a hole in the base. After the blades are retracted (and the delivery tool removed from the site) bone grows into and through the hole in the base, providing extra security in anchoring to the bone.

In other embodiments, a mechanism in the handle may be used to independently retract each blade. E.g., the second blade can be drawn back into the shaft first (or vice versa). A distal end of the shaft provides force to hold the anchor in place while the blades are slid back. The mechanism in the shaft can then retract the first blade.

DETAILED DESCRIPTION OF THE INVENTION

The disclosure provides for bone attachment. Specifically, the disclosure provides systems, devices, and methods useful for attaching an anchor to bone and also useful for attaching a graft or ligament to bone.

Figure 1:
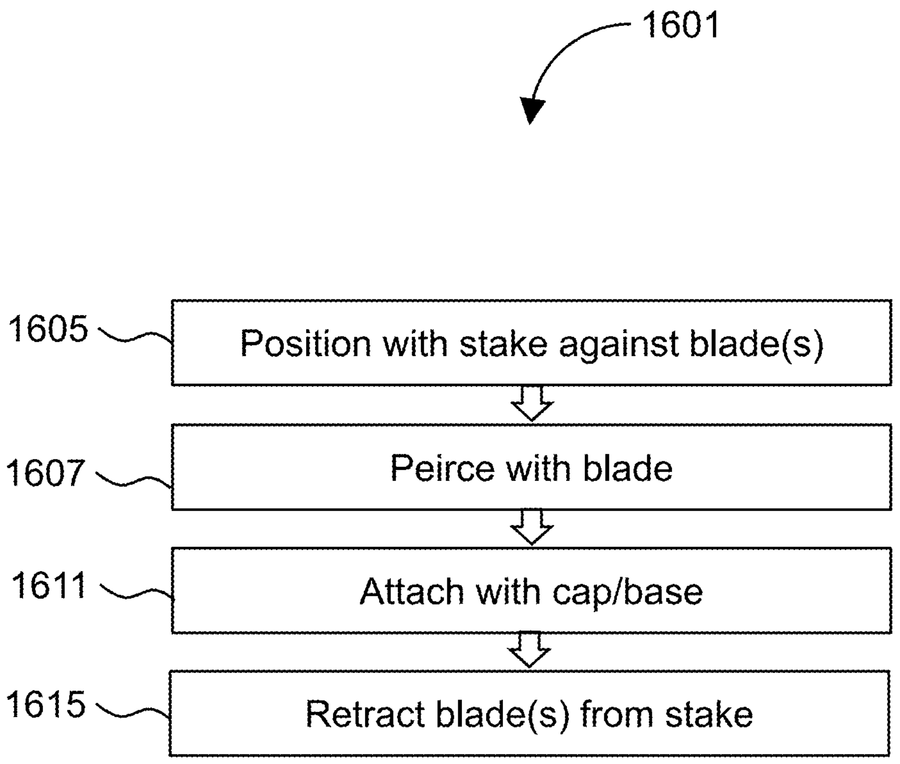
FIG. 1 diagrams steps of a methods 1601 for anchoring a graft or ligament to bone.

FIG. 1 diagrams steps of a methods 1601 for anchoring a graft or ligament to bone. The method 1601 uses a delivery tool with a first blade extending distally from a shaft to a sharpened bone-piercing tip and an implantable bone anchor disposed upon the blade. The bone anchor has a stake extending substantially perpendicular from a base with an open portion in the base through which the first blade of the delivery tool extends.

The method 1601 includes positioning 1605 the tool at the surface of bone. The anchor will be sitting against the blade(s) of the delivery tool (preferred embodiments of the tool have two blades with the stake of the anchor sandwiched therebetween). The tool is used to pierce 1607 the bone. Specifically, the blades of the tool pierce the bone, and this can be done by striking the tool with a mallet.

The blades carry the anchor into the bone and the "base" or "cap" of the anchor attaches 1611 a graft or ligament to the bone. Then, mechanical structures in the handle of the delivery tool retrace 1615 the blades from the stake, and out of the anchor, and away from the bone-leaving the anchor staked into, and attached, to the bone.

Figure 2:
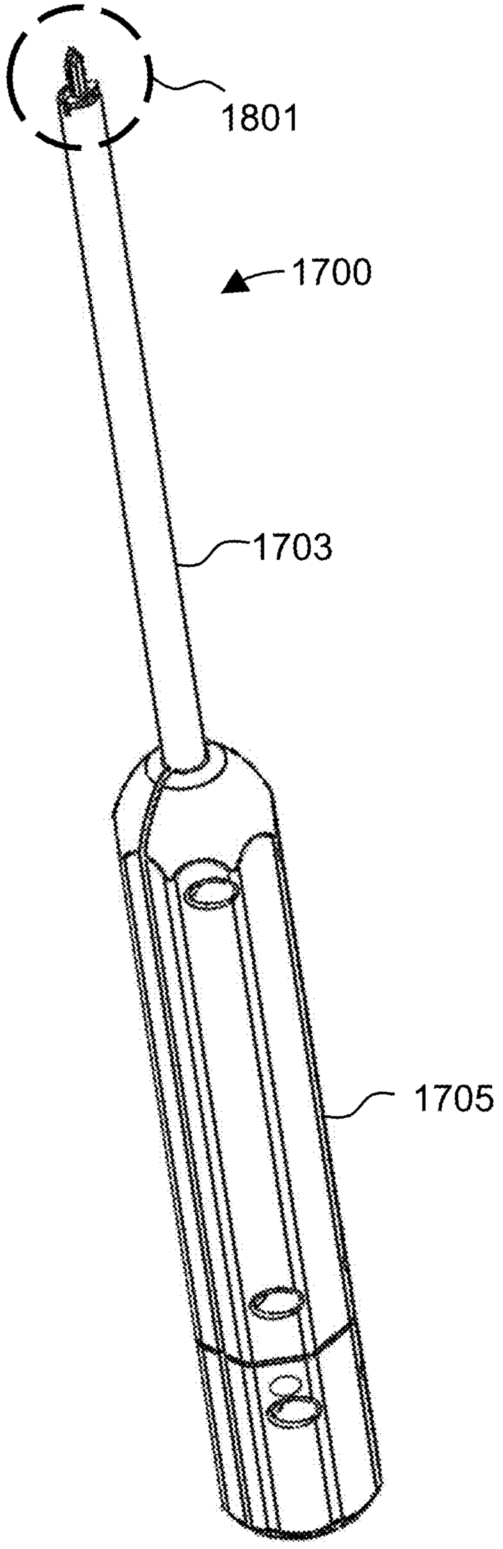
FIG. 2 shows the bone anchor delivery system.

FIG. 2 shows the bone anchor delivery system that includes a delivery tool 1700 and a bone anchor positioned at a delivery tip 1801. Preferably the shaft includes a slidable rod extending therethrough and operable to translate the first blade 1701 between a first, distal position (shown in FIG. 3), wherein the first blade 1701 extends distally from the shaft 1703, and a second, proximal position in which the blade 1701 is retracted proximally into the shaft 1703.

Figure 3:
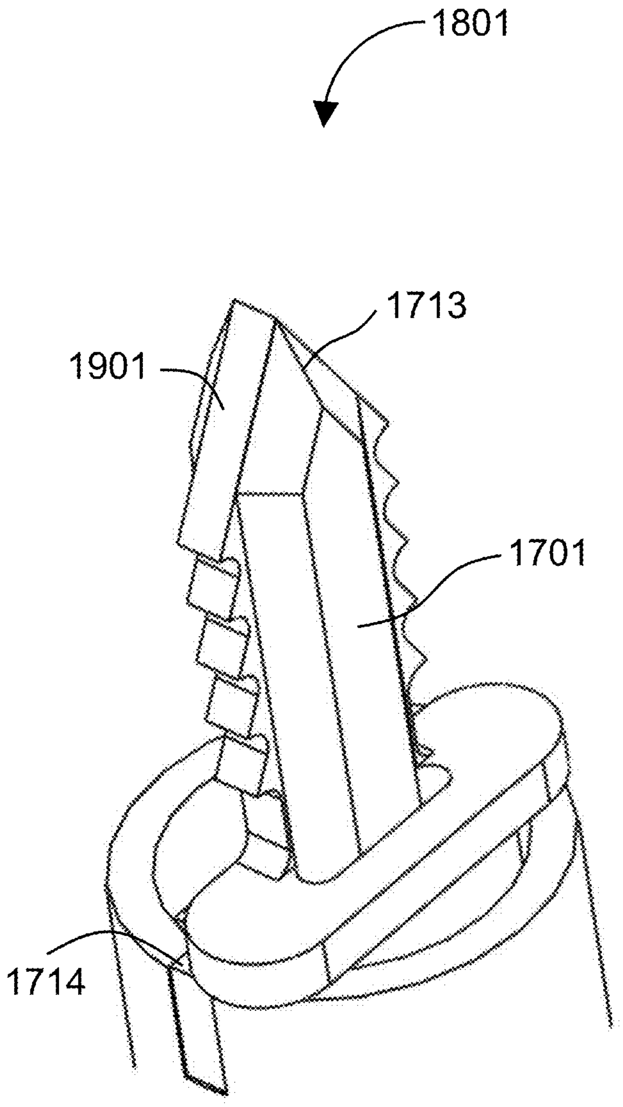
FIG. 3 shows the delivery tip 1801 of the delivery tool.

FIG. 3 shows the delivery tip 1801 of the delivery tool 1701. As shown, the system includes the delivery tool 1701, which includes a handle 1705, an elongated shaft 1703 extending from the handle 1705, and a first blade 1701 extending distally from the shaft to a sharpened bone-piercing tip 1713. The system includes an implantable bone anchor 1901 disposed upon the blade 1701. Here, a distal end of the shaft 1705 has a bridge 1714, which could also be provided as a tab or overhang that sits behind the base of the anchor.

Figure 4:
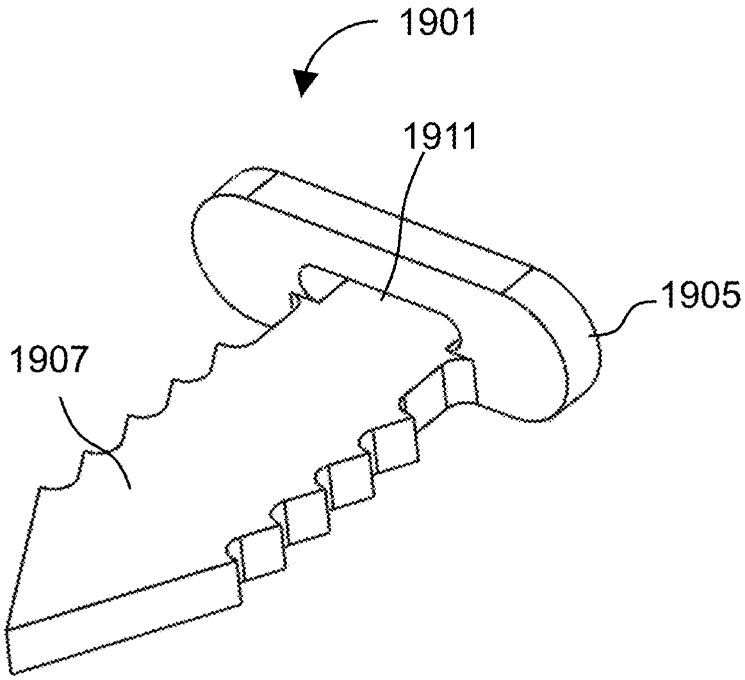
FIG. 4 shows the bone anchor 1901.

FIG. 4 shows the bone anchor 1901. The bone anchor includes a base 1905, a stake 1907 extending substantially perpendicular from the base 1905, and an open portion 1911 in the base through which the first blade 1701 may extend. In some embodiments, the open portion 1911 defines a substantially oval hole through the base 1905, wherein a flat side of the oval hole cooperates with the first substantially planar surface of the stake to define an essentially flat surface against which the first blade lies.

The bone anchor may be made from an absorbable polymer (e.g. PEEK, POM, Nylon, HDPE), bioabsorbable polymer (e.g. PLA, PGA, PDS, PLGA), or a biological metrical such as collagen or bone.

Figure 5:
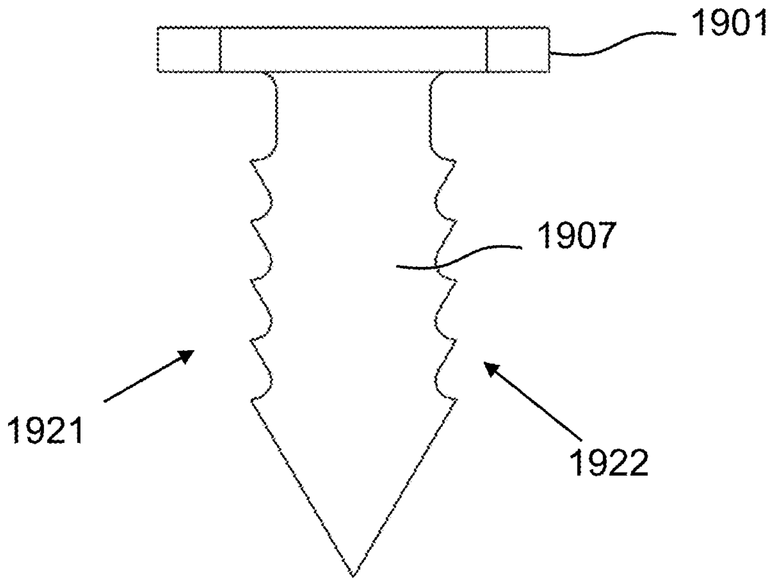
FIG. 5 is a side view of the bone anchor 1901.

FIG. 5 is a side view of the bone anchor 1901. The stake 1907 is substantially flat, comprising first and second opposed substantially planar surfaces and first and second barbed or serrated edges 1921, 1922 where the first and second surface meet and a distal point.

Figure 6:
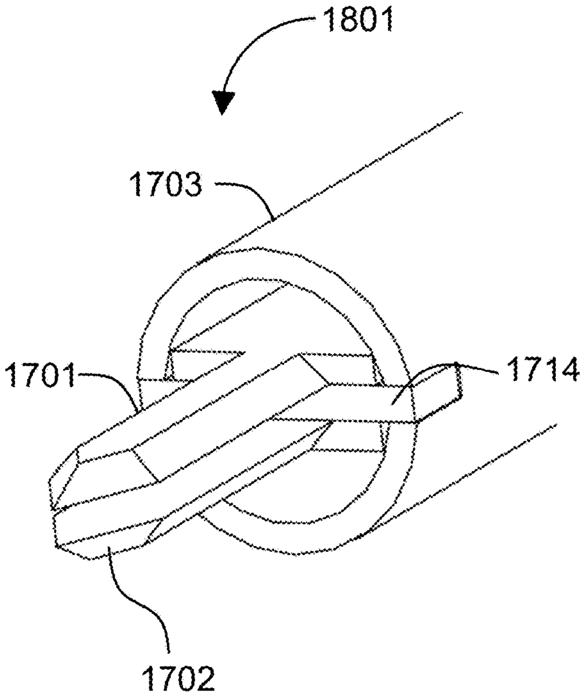
FIG. 6 shows the delivery tip 1801 of the delivery tool.

FIG. 6 shows the delivery tip 1801 of the delivery tool 1701. As shown, the delivery tip includes the first blade 1701 extending distally from the shaft and a second blade 1702. The delivery tool comprises a second blade 1702. The second blade is slidable through the shaft independently of the first blade. As shown, a distal end of the shaft 1705 has a bridge 1714, which could also be provided as a tab or overhang. Preferably, the shaft 1702, the blades 1701, 1702, and the bridge 1714 are a rigid metal such as stainless steel. In some embodiments, the bridge 1714 is welded to the shaft 1703.

Figure 7:
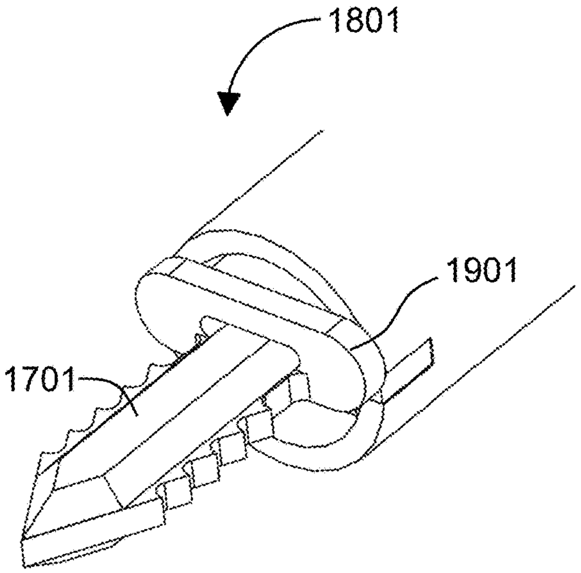
FIG. 7 shows the delivery tip with the implantable bone anchor.

FIG. 7 shows the delivery tip with the implantable bone anchor 1901 disposed upon the blade 1701. A flat side of the first blade 1701 lies against the first substantially planar surface of the stake 1907 of the bone anchor 1901. In some embodiments, the first and second blades comprise a rigid metal, wherein the bone anchor comprises a pliable material, which may be a polymer, natural material, or a bio-absorbable material. The first and second blades 1701, 1702 prevent the bone anchor 1901 from deforming during delivery. The bridge 1714 sits behind the base of the anchor. When the blades 1701, 1702 are retracted, the bridge 1714 keeps the anchor sitting in the bone. After the blades are retracted in the shaft, the device 1700 can be carried way from the surgical site, leaving only the anchor 1901 in the bone.

Figure 8:
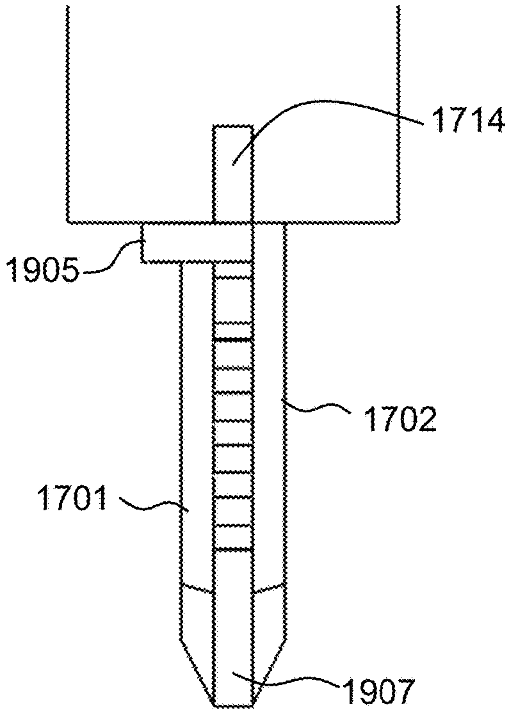
FIG. 8 shows the bone anchor 1901 on the delivery tip.

FIG. 8 shows the bone anchor 1901 on the delivery tip 1801 with the stake 1907 sandwiched between the first blade 1701 and the second blade 1702. The first and second blade 1701, 1702 sit against respective opposed surfaces of the stake 1907 of the bone anchor.

As shown in FIG. 7 and FIG. 8, when the first blade 1701 and the second blade 1702 are in distal positions with the stake 1907 of the bone anchor therebetween, the first blade 1701, the second blade 1702, and the stake 1907 cooperate to present a sharpened tapered tip useful to pierce into bone. This configuration provides the mechanism by which the polymer (e.g., pliable) anchor may be driven into bone, even bone that has not had a pilot hole pre-drilled.

Figure 9:
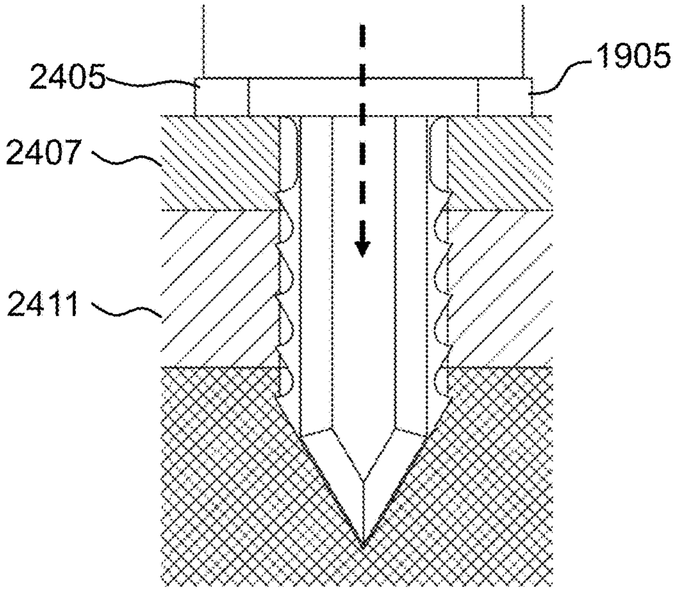
FIG. 9 shows the blades 1701, 1702 piercing the bone.

FIG. 9 shows the blades 1701, 1702 piercing the bone to make the hole, carrying the anchor 1901 into the bone with them. Preferably, the base 1905 of the bone anchor comprises overhangs 2405 that extend away from the stake 1907 in multiple directions. By those overhangs 2405, the bone anchor 2101 can hold a graft 2407 onto bone 2411. When the bone anchor 1901 is passed through a graft 2407 or ligament and into bone 2411, the overhangs 2405 hold the graft 2407 or ligament against the bone 2411.

Figure 10:
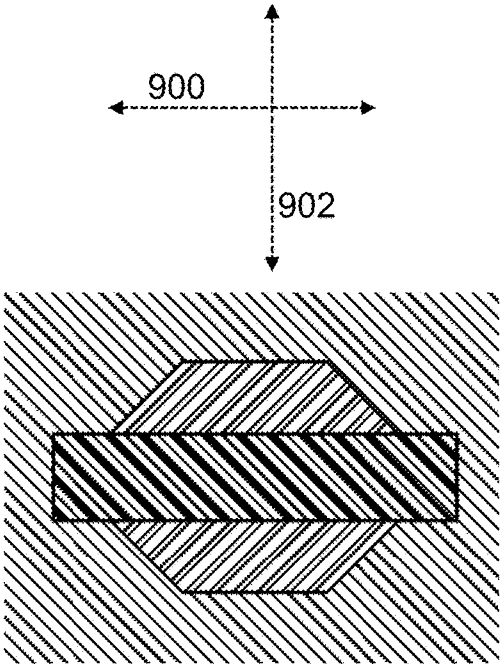
FIG. 10 is a diagram of the cross-sectional area of the stake and the blades.

FIG. 10 is a diagram of the cross-sectional area of the stake and the blades. The image illustrates an important principle. The bone anchor 2101 maximizes grip along an attachment axis 900. The delivery blades 1701, 1702 displace tissue along a blade axis 900. The maximum tissue displacement by the tool (along the blade axis 902) and the maximum grip by the anchor 1201 (along the attachment axis 900) are in different directions and, preferably, the attachment axis 900 is orthogonal to blade axis 900 (substantially or completely). It is also noted that the blades 1701, 1702 are preferably flat and are not, themselves, hemi-tubular (like a puncturing cannula). The flat blades and the orientation of the axes maximizes possible grip of the anchor 1201 into bone.

Figure 11:
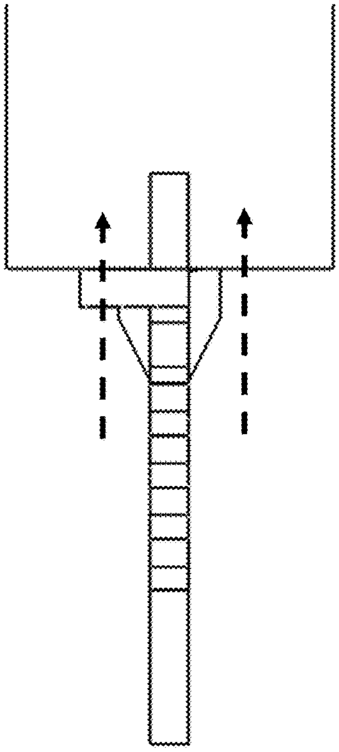
FIG. 11 shows the blades 1701, 1702 retracing into the shaft.
Figure 12:
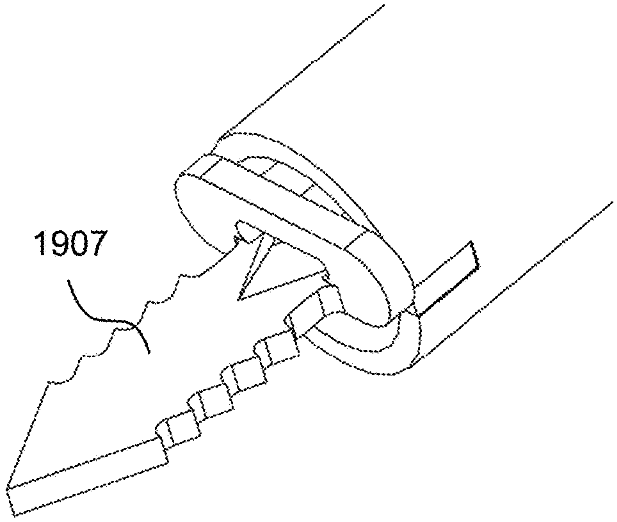
FIG. 12 is a perspective view of the blades 1701, 1702 retracing into the shaft.

FIG. 11 shows the blades 1701, 1702 retracing into the shaft 1703. Preferably the first and second blades are independently slidable away from the sharpened tapered tip in a proximal direction into the elongated shaft to leave the implantable bone anchor uncoupled from the delivery tool FIG. 12 is a perspective view of the blades 1701, 1702 retracing into the shaft 1703. As depicted, the stake 1907 of the bone anchor has a plurality of teeth along first and second edges.

Figure 13:
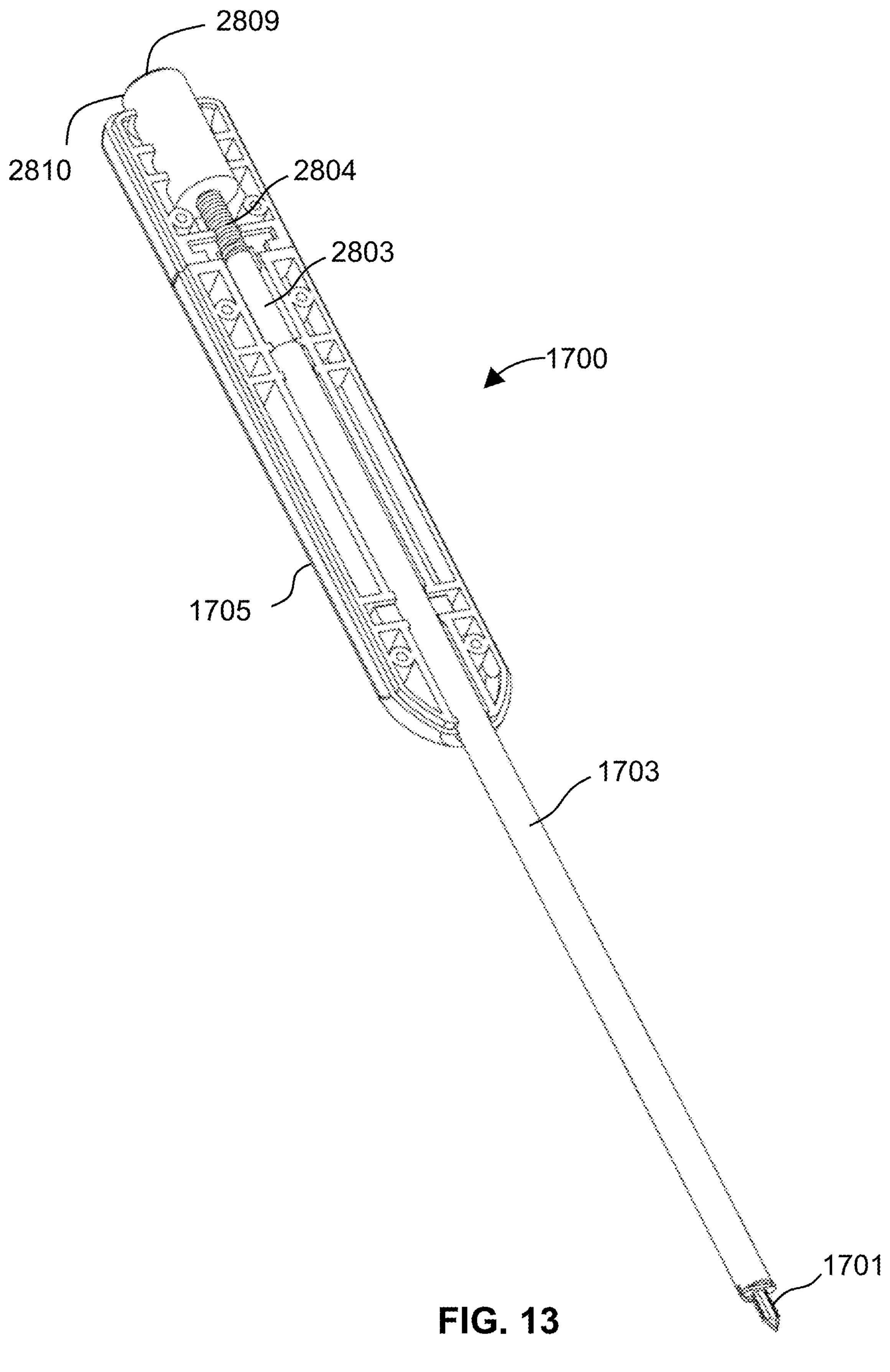
FIG. 13 is a cutaway of the delivery tool.

FIG. 13 is a cutaway of the delivery tool 1700, showing mechanisms of the tool 1700. The shaft 1703 includes a slidable rod 2803 extending therethrough operable to translate the first blade 1701. Preferably, a proximal end of the handle 1705 presents a flat or solid head surface 2809. When the sharpened tapered tip is positioned against bone and the flat or solid head surface 2809 is hammered with a mallet, the sharpened tapered tip pierces a hole in the bone and the delivery tool carries the bone anchor into the bone down to the base. Preferably, the delivery tool has a pair of blades 1701, 1702 that extend from the rod 2803 that extends from the handle 1705 and through the shaft 1703 of the device 1700. The bone anchor is carried between the two blades.

A distal portion of the shaft 1702 may optionally be covered by a sleeve (not pictured). The sleeve may be a plastic or elastic material with a tapered tip and may include a split into the tapered tip, so that the tapered tip defines to semi-conical portions that allow the distal tip to bend open when the sleeve is retracted over the shaft 1703. A sleeve may provide important safety and utility benefits by protecting handles from the sharped blades 1701, 1702 and also keeping the anchor 1201 in place from unpackaging up until delivery.

A surgeon can navigate the shaft through a surgical incision or cannula and position the anchor at a target sit over bone (and over a graft positioned on the bone). The surgeon can drive the blades (and the carried anchor) into the bone, which may be accomplished by tapping the surface 2809 at the base of the handle with a mallet.

The handle also includes a mechanism to retract the blades into the handle. The mechanism preferably include a threaded fitting 2804 around a base of the rod wherein a knob 2810 exposed at the handle can be turned to withdraw the blades into the handle via a screw drive provided by the threaded fitting. A distal end of the shaft has a bridge, tab, or overhang that sits behind the base of the anchor. As the surgeon screws the knob, the bridge, tab, or overhang keeps the anchor sitting in the bone while the blades are withdrawn slowly and gently into the shaft (leaving only the anchor in the bone).

The depicted structures use the bridge 1714 to hold the anchor 1201 in position while the device is removed from the site. After the surgeon hammers the back surface 2809, puncturing the bone with the blades 1701, 1702 and placing the anchor in the resulting opening, the anchor will hold best with very gently removal of the device 1700 that does not impart any sudden shocks and does not "wiggle" the anchor in the bone. The surgeon turns the knob 2810 to, via a screw drive, draw the blades back slowly and gently. The bridge 1714 holds the anchor. This mechanism avoid shocks or fine motions that compromise attachment strength. The surgeon can push forward (towards bone) with the handle 1705 while operating the screw drive, to hold the anchor 1201 firmly and still. The blades only leave voids along the blade axis 902 and do not make extensive voids (and in fact leave no voids) beyond the anchor 1201 along the attachment axis 900.

Figure 14:
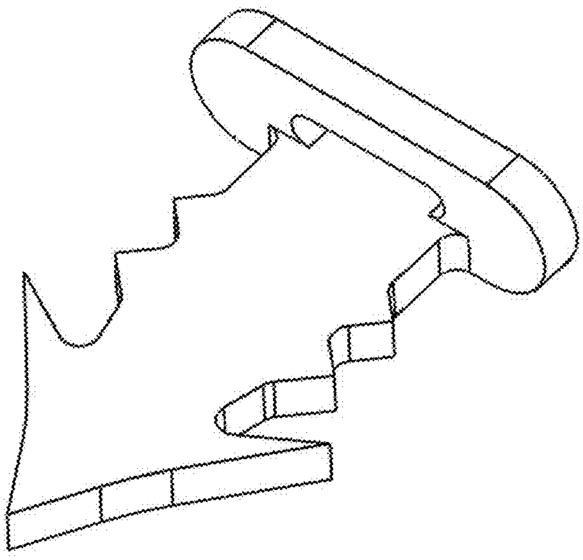
FIG. 14 is another embodiment of a bone anchor, with widely flanged barbs

FIG. 14 is another embodiment of a bone anchor, with widely flanged barbs

Figure 15:
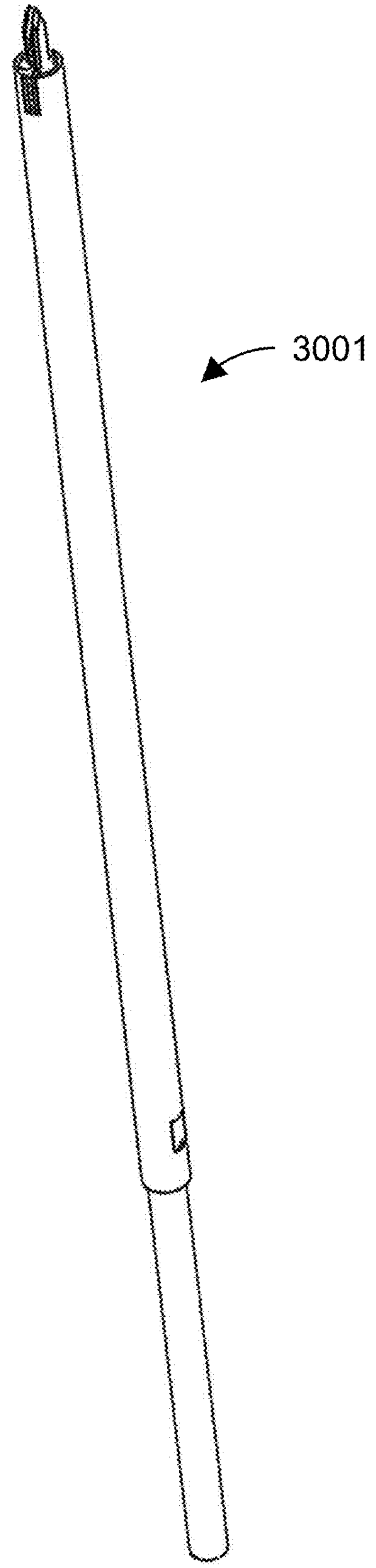
FIG. 15 is another embodiment of a delivery tool 3001.

FIG. 15 is another embodiment of a delivery tool 3001.

Figure 16:
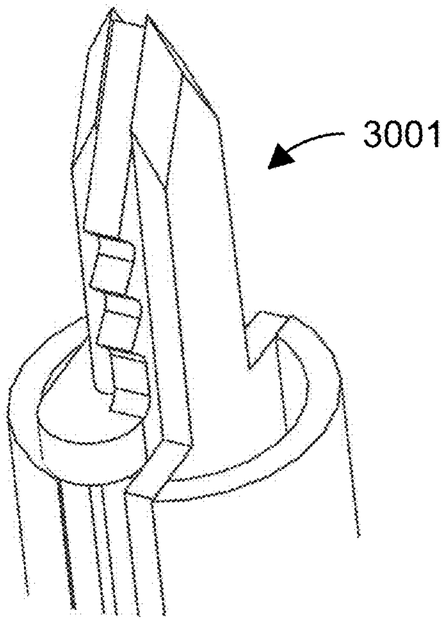
FIG. 16 shows a loaded delivery tip of the delivery tool 3001.

FIG. 16 shows a loaded delivery tip of the delivery tool 3001.

Figure 17:
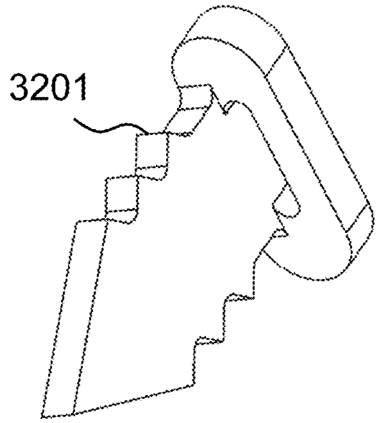
FIG. 17 shows another embodiment of a bone anchor.

FIG. 17 shows another embodiment of a bone anchor.

Figure 18:
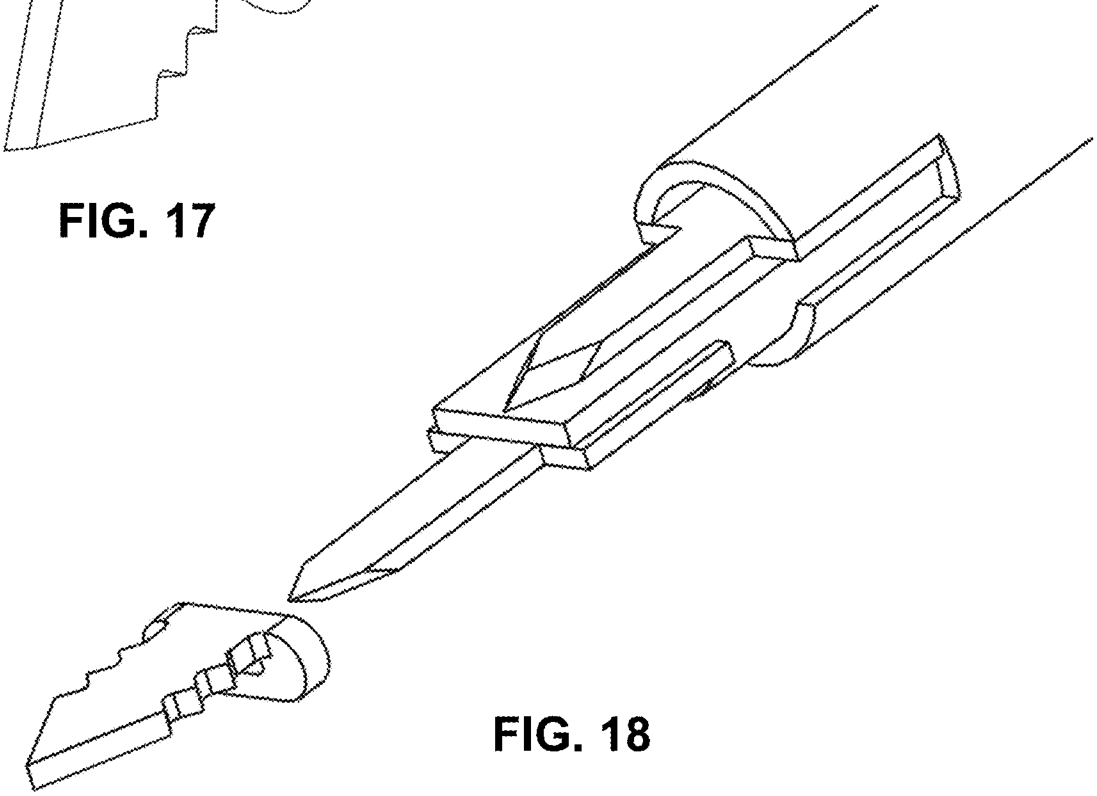
FIG. 18 illustrates the independent translation of blades.

FIG. 18 illustrates the independent translation of blades 1701, 1702 of the delivery tool 1700, releasing from an anchor 3201. This embodiment may be used with any of the anchor shown herein.

Figure 19:
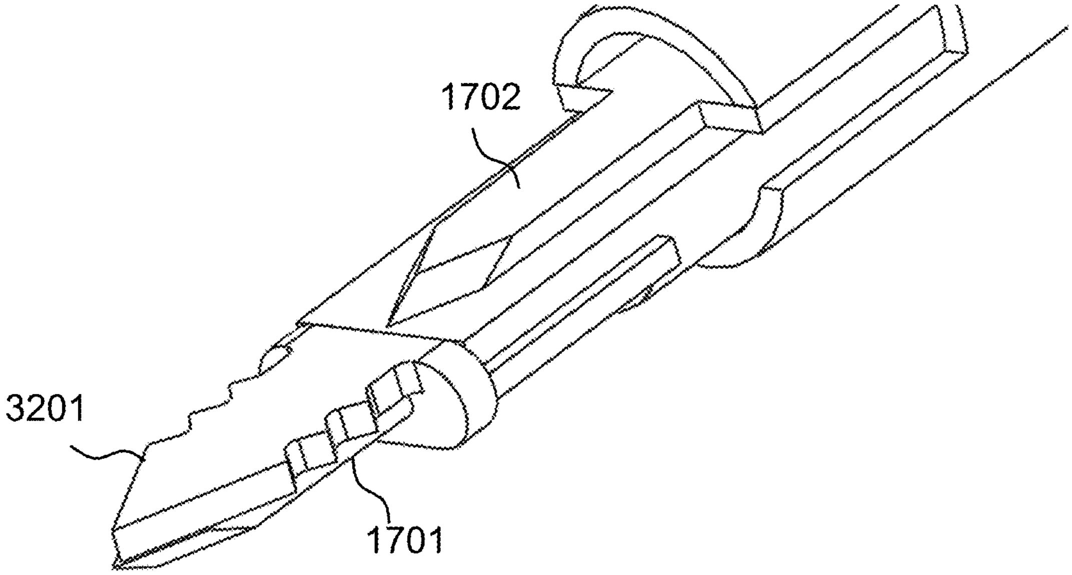
FIG. 19 shows the anchor 3201 loaded on the blade 1701 of the tool 1700.

FIG. 19 shows the anchor 3201 loaded on the blade 1701 of the tool 1700.

Figure 20:
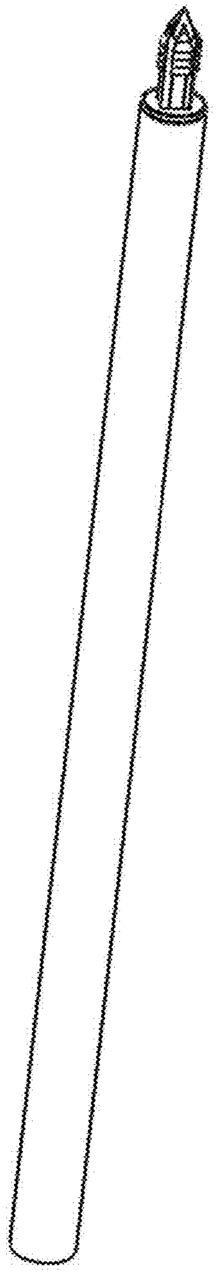
FIG. 20 shows another embodiment with a ridged bone anchor on a delivery tool.

FIG. 20 shows another embodiment with a ridged bone anchor on a delivery tool.

Figure 21:
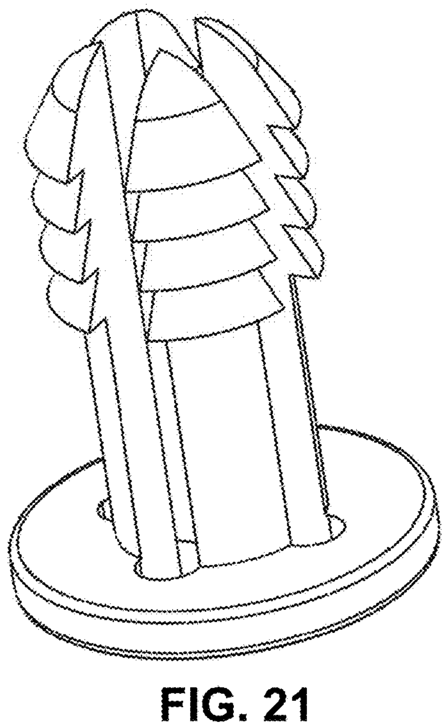
FIG. 21 shows the ridged bone anchor.

FIG. 21 shows the ridged bone anchor.

Figure 22:
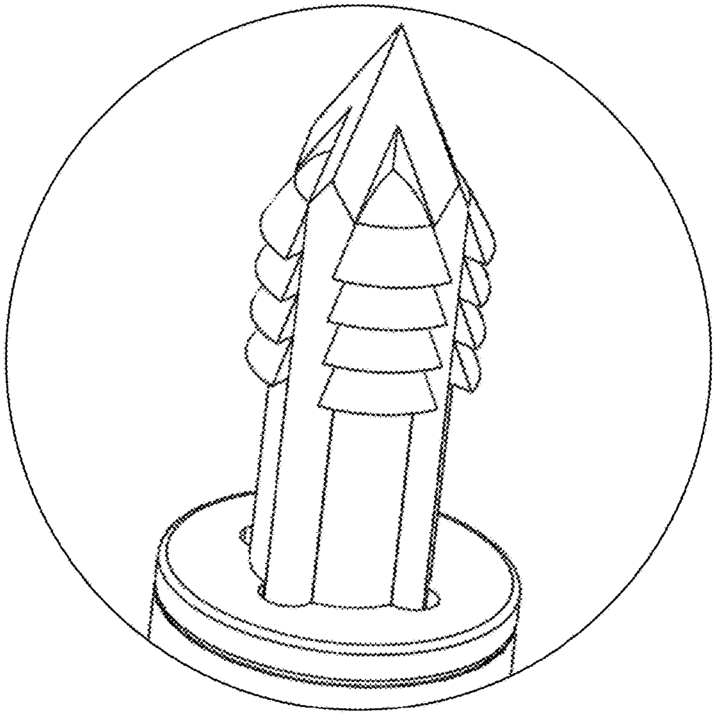
FIG. 22 is a detail view of the ridges bone anchor.

FIG. 22 is a detail view of the ridges bone anchor.

Figure 23:
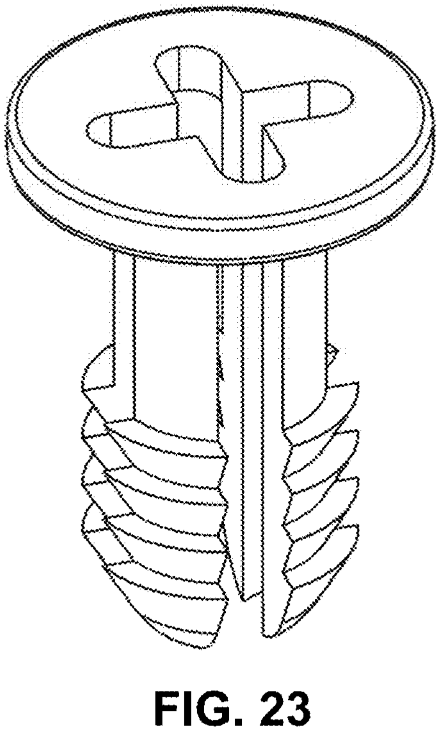
FIG. 23 is a top view of the ridged bone anchor.

FIG. 23 is a top view of the ridged bone anchor.

Figure 24:
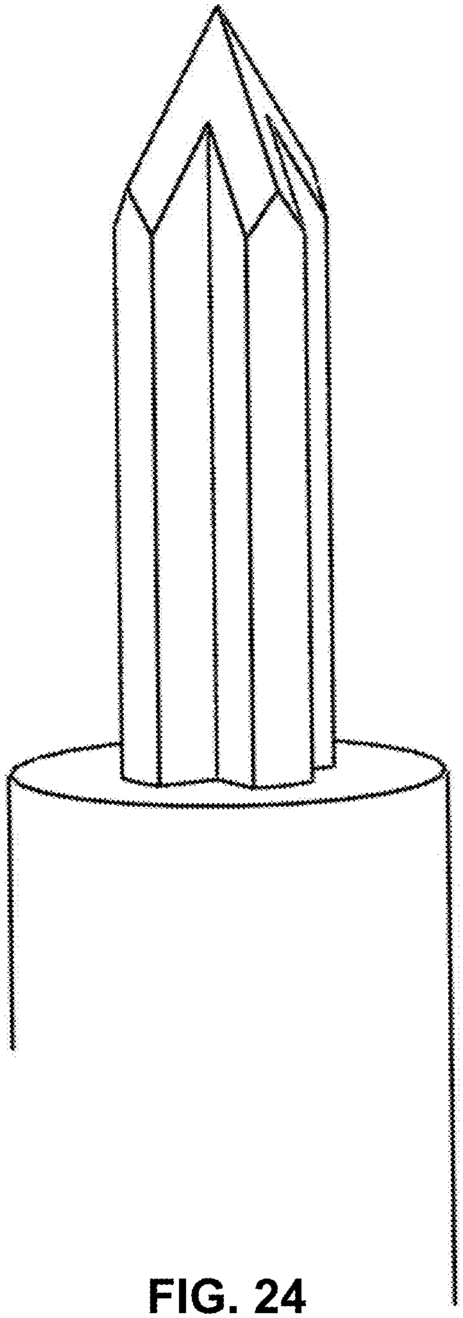
FIG. 24 is a detail view of a delivery tip of a tool for delivering the ridged bone anchor.

FIG. 24 is a detail view of a delivery tip of a tool for delivering the ridged bone anchor.

Figure 25:
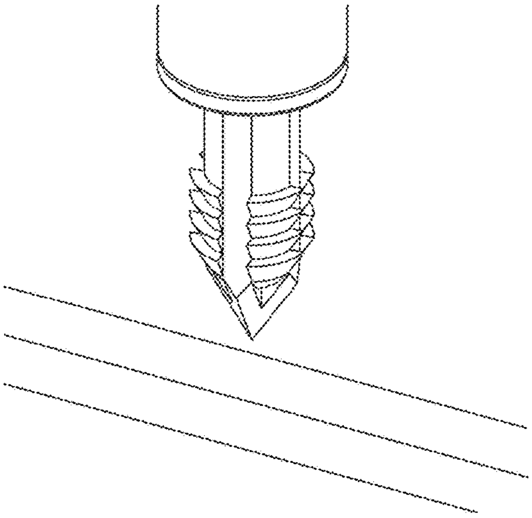
FIG. 25 shows use of the tool to bring the ridged bone anchor to a bone.

FIG. 25 shows use of the tool to bring the ridged bone anchor to a bone.

Figure 26:
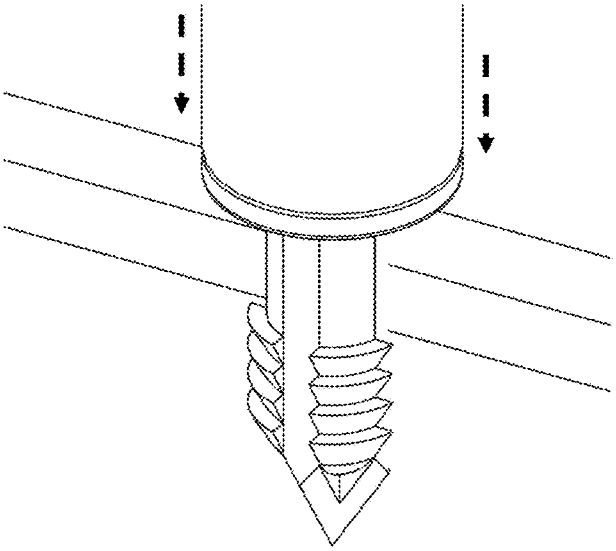
FIG. 26 shows piercing a graft and bone with the tool carrying the ridged bone anchor.

FIG. 26 shows piercing a graft and bone with the tool carrying the ridged bone anchor.

Figure 27:
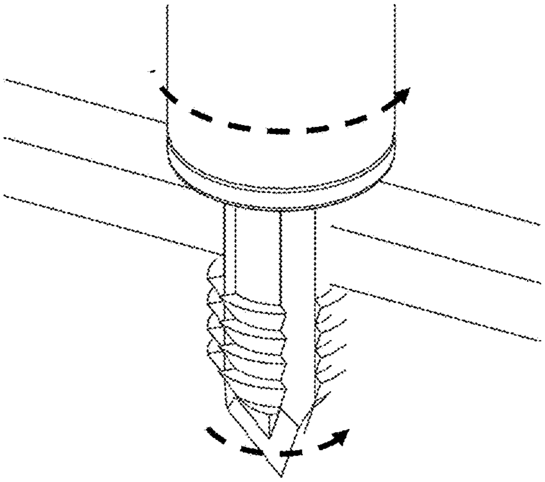
FIG. 27 shows rotating the tool.

FIG. 27 shows rotating the tool about 45 degrees to lock ridges of the ridged bone anchor into surrounding bone.

Figure 28:
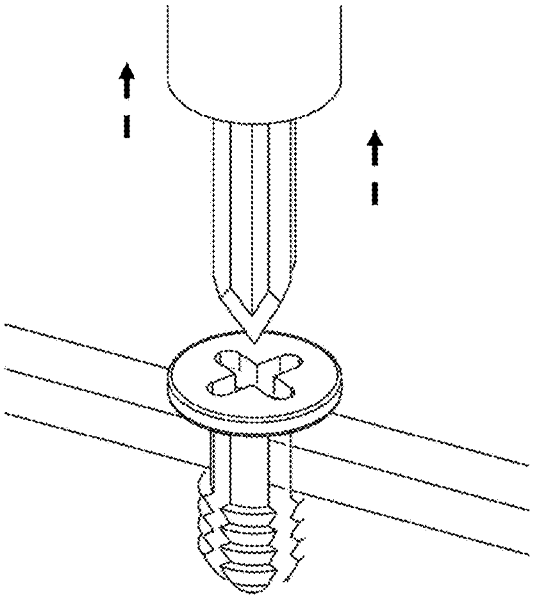
FIG. 28 shows removing the tool.

FIG. 28 shows removing the tool, leaving the ridged bone anchor holding a graft onto bone.

Figure 29:
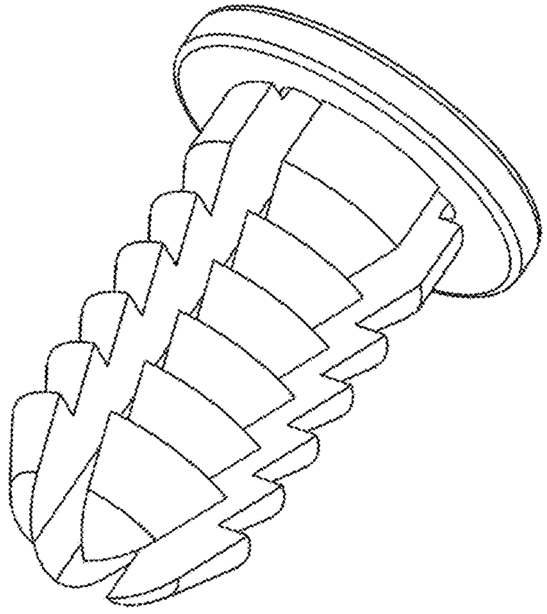
FIG. 29 shows a gently-tapered embodiment of the ridged bone anchor.

FIG. 29 shows a gently-tapered embodiment of the ridged bone anchor.

Figure 30:
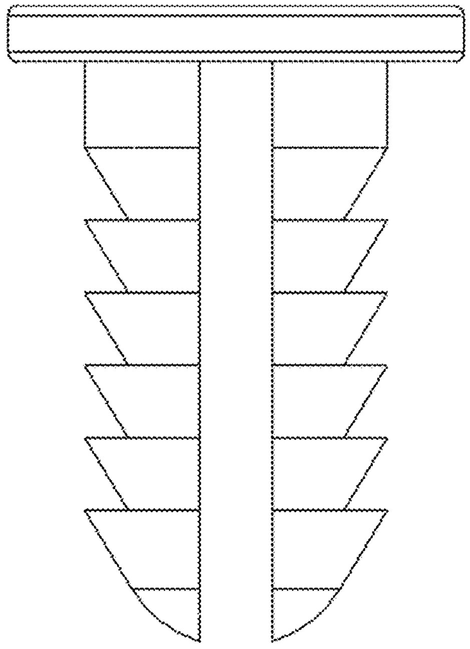
FIG. 30 is a side view of the gently-tapered embodiment of the ridged bone anchor.

FIG. 30 is a side view of the gently-tapered embodiment of the ridged bone anchor.

Figure 31:
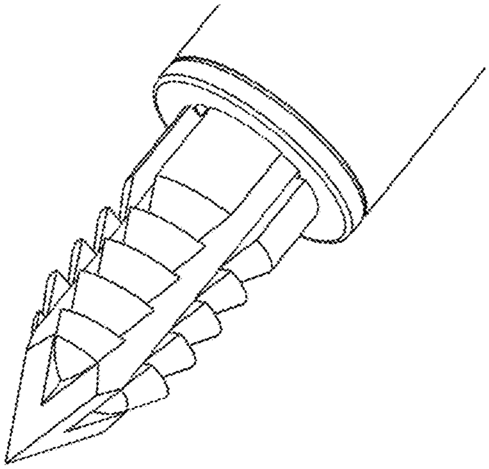
FIG. 31 is a helical embodiment of the ridged bone anchor.

FIG. 31 is a helical embodiment of the ridged bone anchor.

Figure 32:
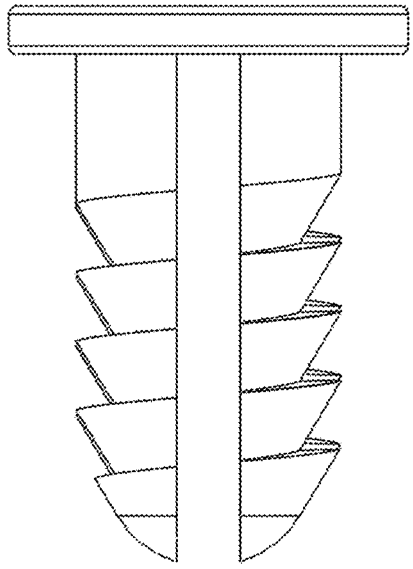
FIG. 32 is a side view of the helical embodiment of the ridged bone anchor.

FIG. 32 is a side view of the helical embodiment of the ridged bone anchor.

Figure 33:
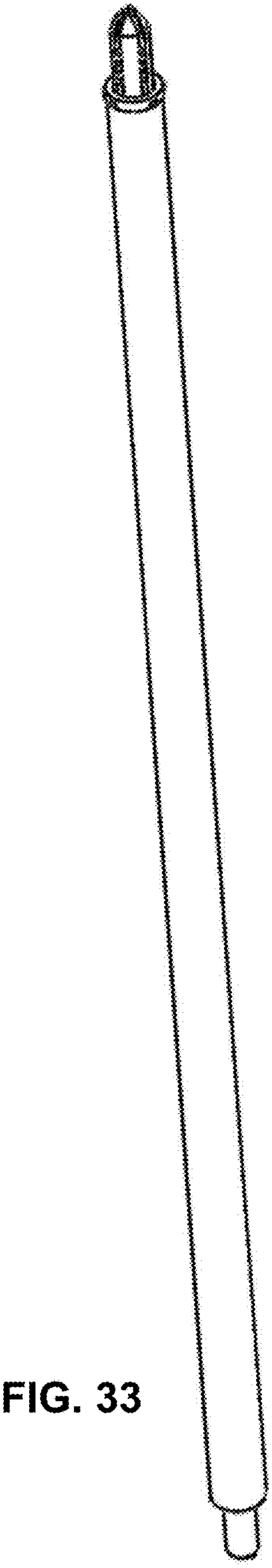
FIG. 33 is multi-pronged tool.

FIG. 33 is multi-pronged tool for delivering a ridged bone anchor of another embodiment.

Figure 34:
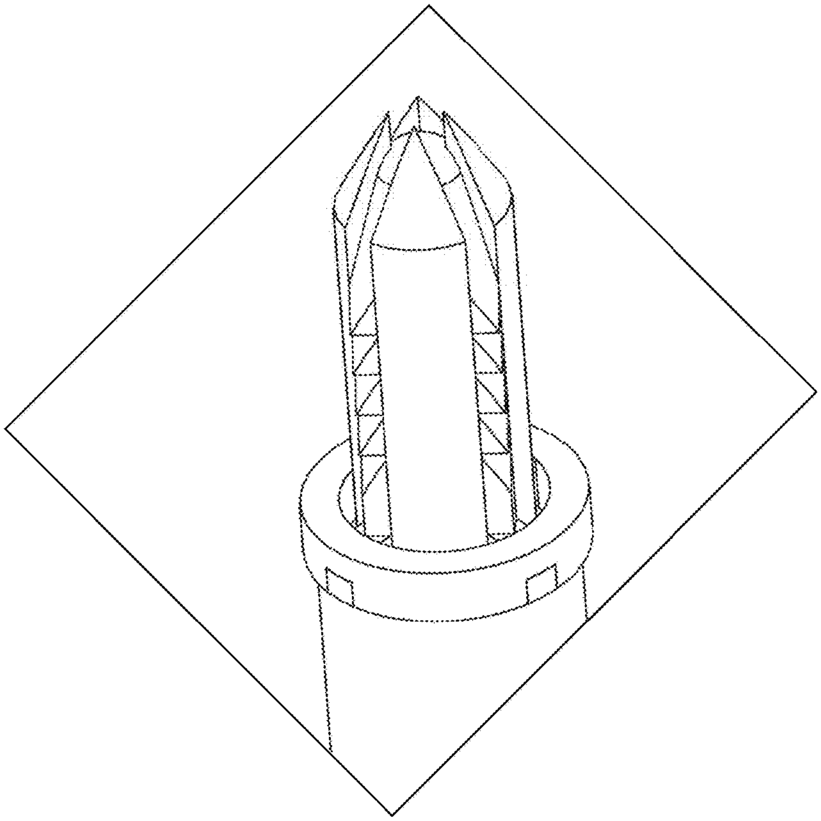
FIG. 34 is a detail view of a delivery tip of the multi-pronged tool.

FIG. 34 is a detail view of a delivery tip of the multi-pronged tool showing extended spikes covering and carrying the ridged bone anchor.

Figure 35:
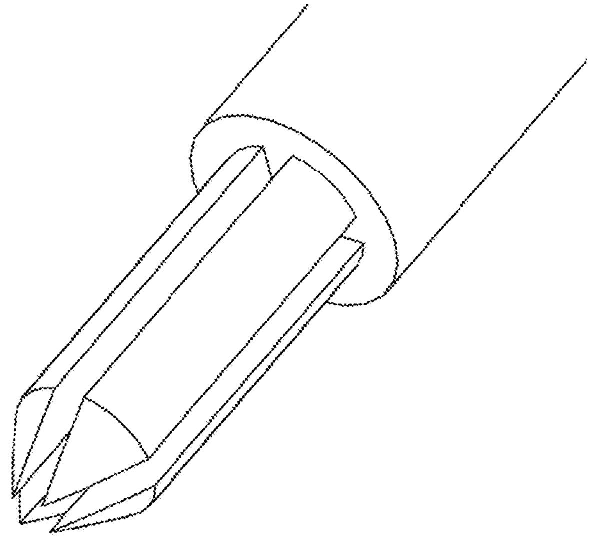
FIG. 35 is a detail view of a delivery tip.

FIG. 35 is a detail view of a delivery tip of the multi-pronged tool without the anchor being in the picture.

Figure 36:
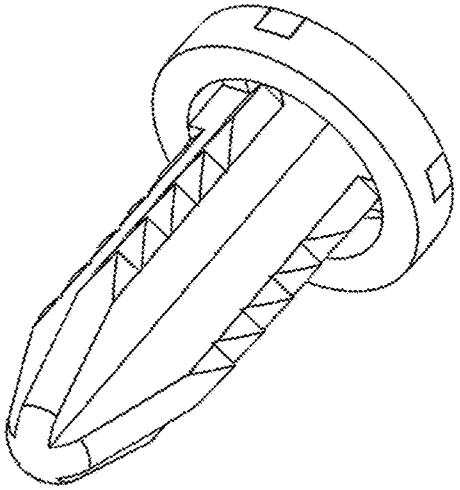
FIG. 36 shows a ridged bone anchor.

FIG. 36 shows a ridged bone anchor designed to fit within the spikes of the multi-pronged tool.

Figure 37:
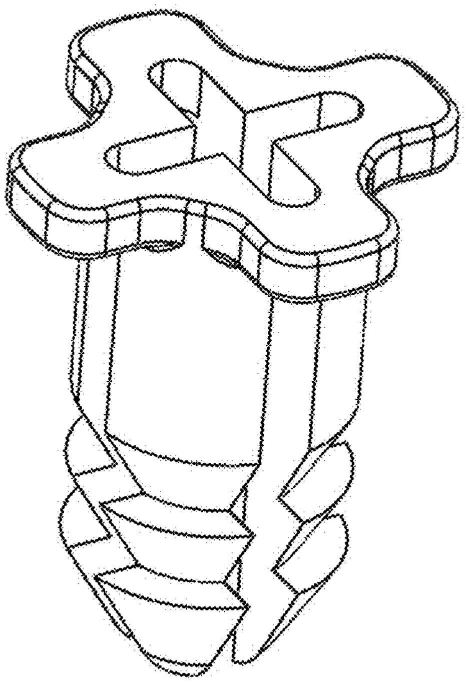
FIG. 37 shows an embodiment of the bone tack with a cross shaped cap.

FIG. 37 shows an embodiment of the bone tack with a cross shaped cap. The cross-shaped design reduce the total cross section of the implant toward the top and reduce the total foreign matter mass, which may help to reduce inflammation.

Figure 38:
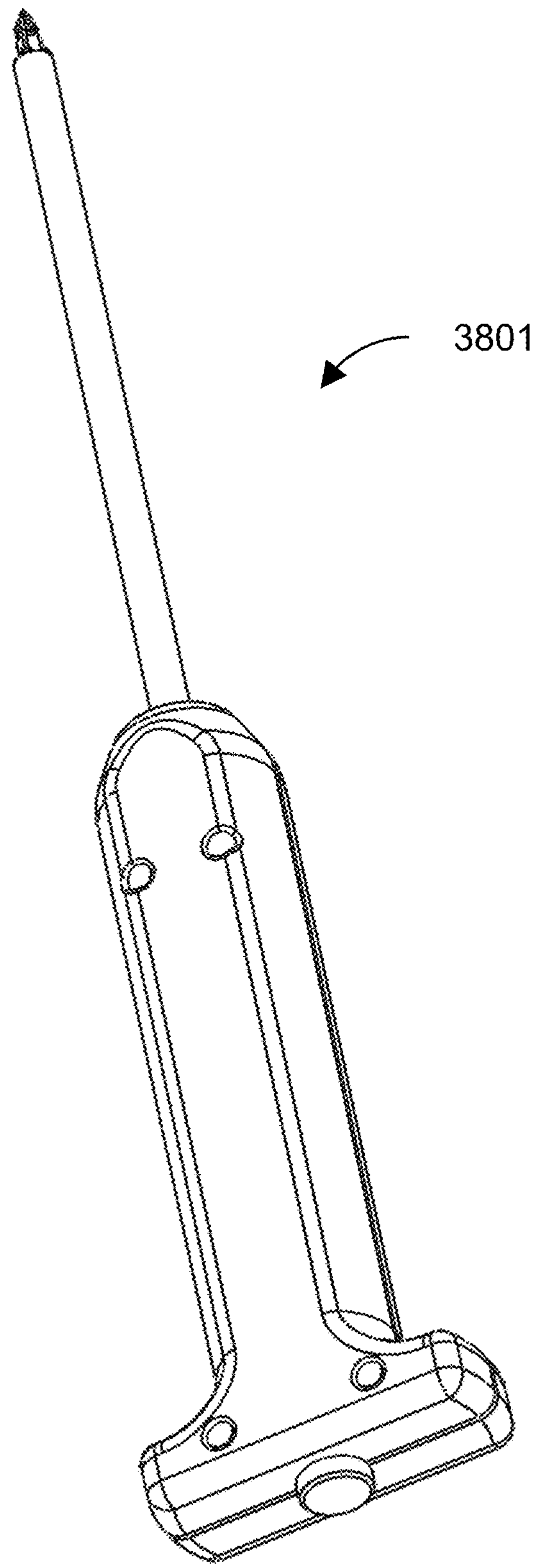
FIG. 38 shows a bone anchoring device with T-shaped handle.

FIG. 38 shows an embodiment of the bone anchoring device 3801, including a handle with a T-shaped proximal portion, a saft extending from a distal portion of the handle, and a driver tip at the distal end of the shaft. The handle allow rotation and pulling (since it is T shaped) and also include a metallic striking cap, directly connected to the shaft.

As discussed above, embodiments of the disclosure may include a sleeve covering a shaft of a bone anchor delivery tool.

Figure 39:
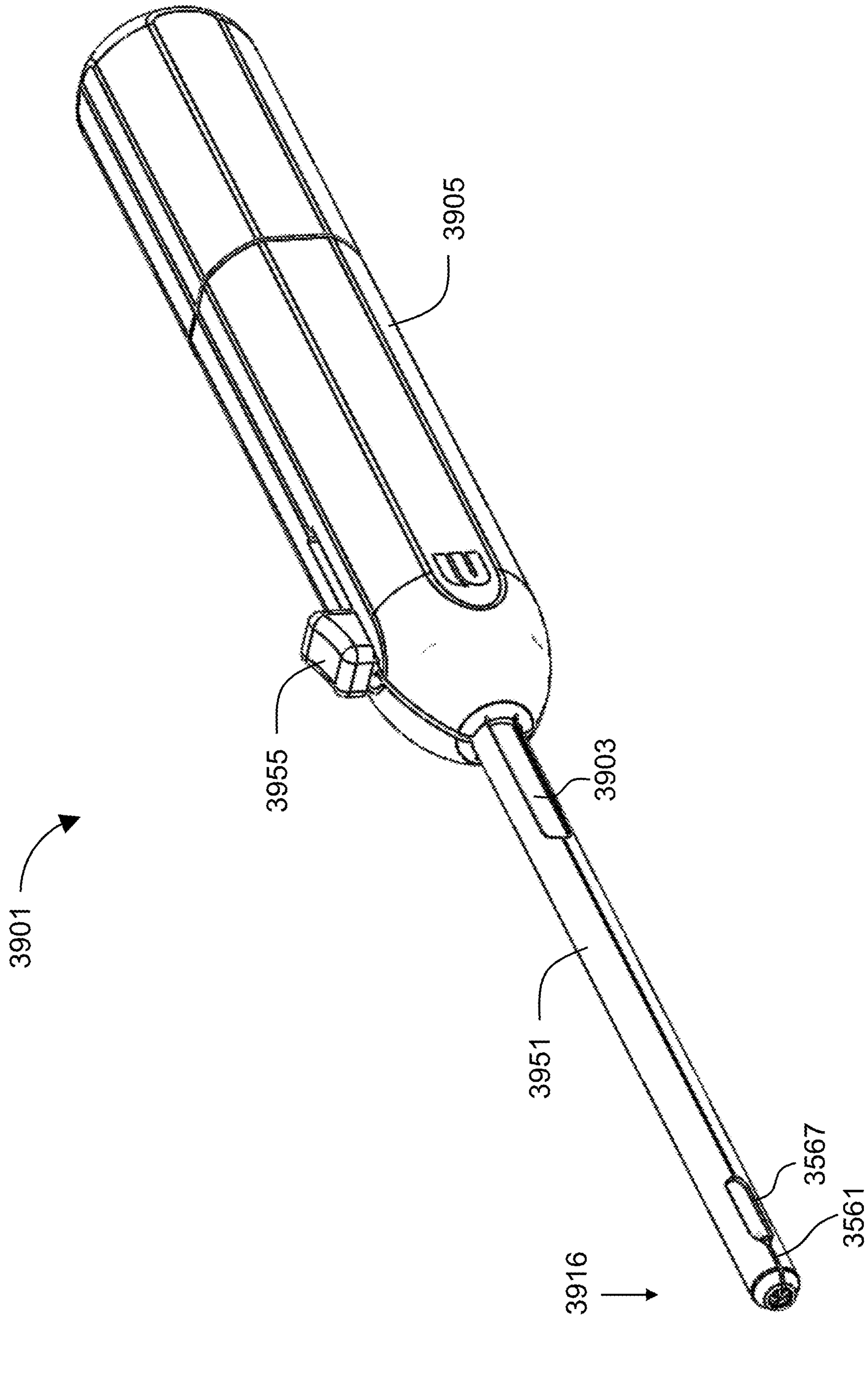
FIG. 39 shows a bone anchor delivery tool with a slider knob.

FIG. 39 shows a bone anchor delivery tool 3901 with an insertion sleeve 3951 covering the shaft 3903 that extends from the handle 3905. A bone anchor is positioned at a delivery tip 3916 of the delivery tool 3901 but is not visible in the figure due to the insertion sleeve 3951. Preferably the shaft 3903 includes a slidable rod extending therethrough and operable to translate a first blade between a first, distal position (similar to what is shown in FIG. 3), wherein the first blade extends distally from the shaft 3903, and a second, proximal position in which the blade is retracted proximally into the shaft 3903.

The insertion sleeve 3951 facilitates insertion of the delivery tip 3916 of the delivery tool 3901 through an incision or a cannula. In addition, the sleeve 3951 covers a fastener at the delivery tip 3916 of the device, keeping the fastener from being dislodged from the device 3901 during the insertion.

As shown, a slit 3651 extends into, and bifurcates, the distal end of the insertion sleeve 3951. The slit 3651 may extend to, and open into, an open cutaway 3567 (e.g., replicated on both lateral sides of the insertion sleeve 3951). The insertion sleeve 3951 is preferably made of a deformable, e.g., elastic, material such as a polymer such as a polyurethane. The open cutaways 3567, by removing material from portions of the sleeve, create effective hinges, allowing the two opposed semi-circumferential ends of the distal end of the insertion sleeve 3951 to “open”, i.e., bend away from one another.

The movement of the insertion sleeve 3951 may be controlled by the surgeon by a slider knob 3955, located at the top portion of the handle 3905. When the insertion sleeve 3951 is located fully forward (in a distal-most position), the insertion sleeve 3951 is locked in place in order to facilitate insertion through an incision without the risk of the sleeve sliding back during insertion. Once the delivery tip 3916 has been inserted through an incision (optionally through a cannula positioned there) and brought into proximity with a surgical site, the surgeon may retract the insertion sleeve 3951 by pressing the slider knob 3955 and fulling in backwards, in a proximal direction.

Figure 40:
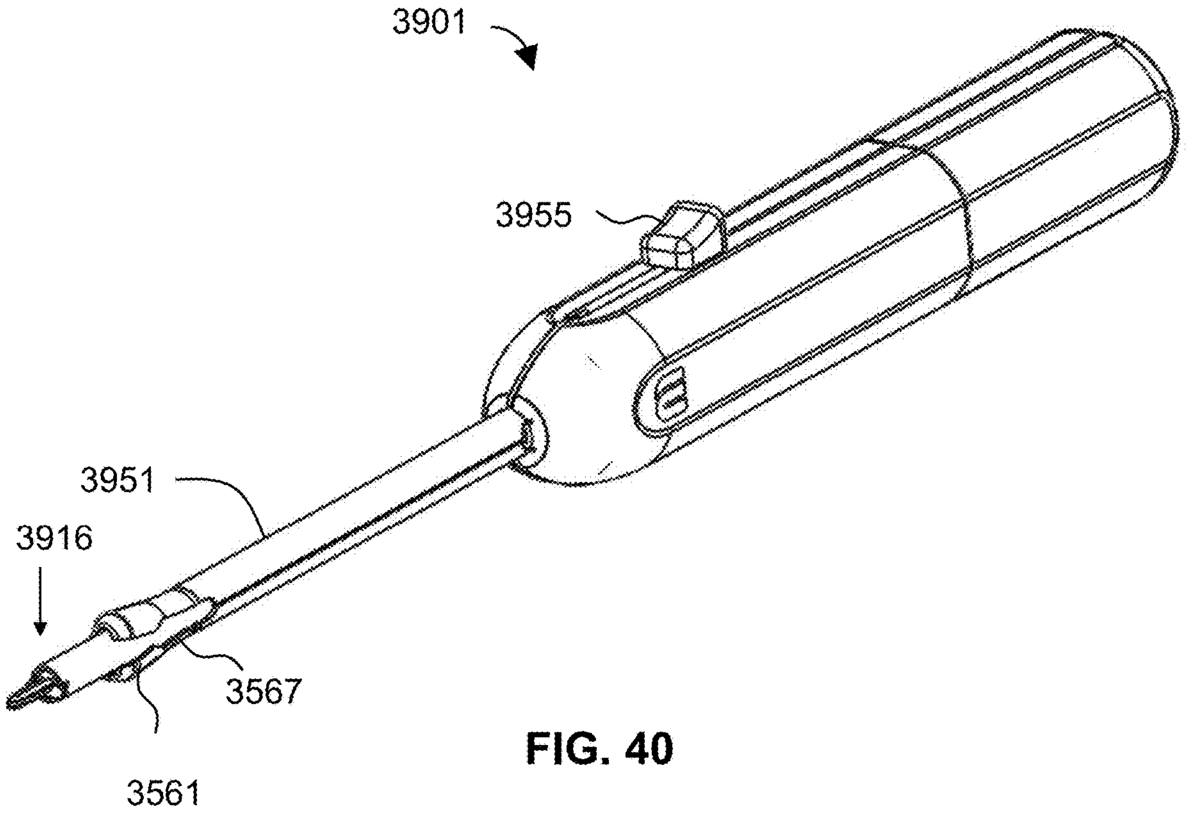
FIG. 40 shows the delivery tool with slider knob with the insertion sleeve retracted.

FIG. 40 shows the device 3901 with the insertion sleeve 3951 retracted. To have the insertion sleeve 3951, the surgeon has pushed the slider knob 3955 down, releasing a slide-lock, and pulled, or slid, the slider knob 3955 back, in a proximal direction. Because the insertion sleeve 3951 has been brought back, in a proximal direction, a distal end of the insertion sleeve 3951 has had to open to accommodate the shaft 3903. As shown, the slit 3651 and the open cutaways 3567 allow the sleeve to open.

Figure 41:
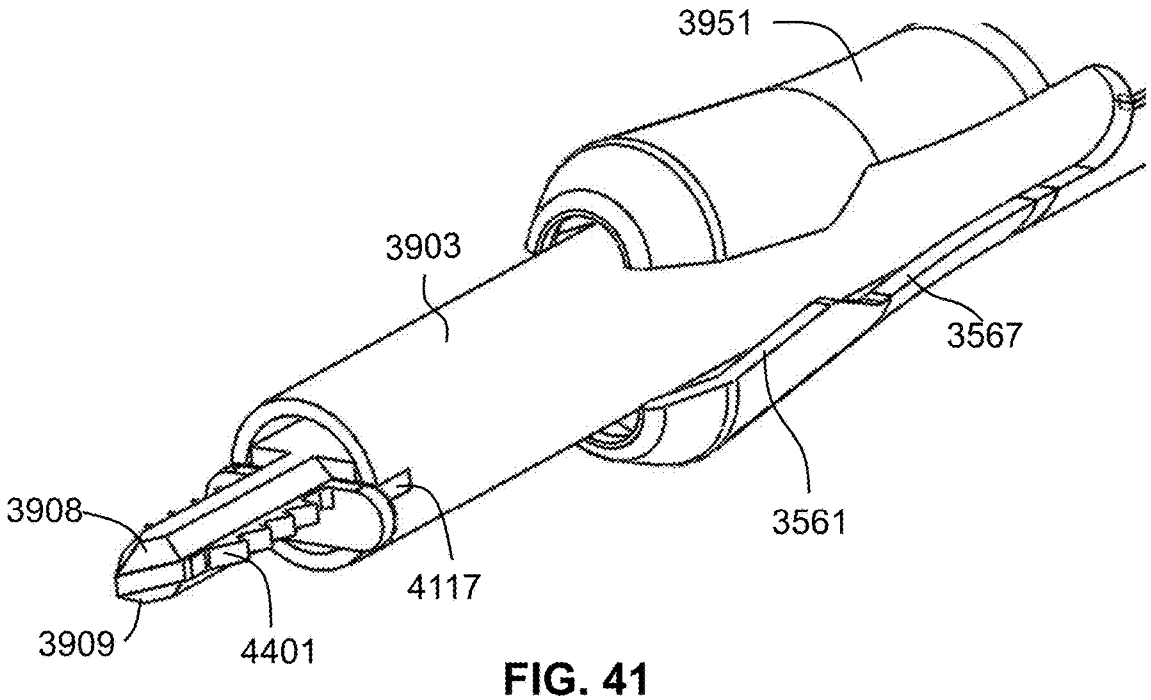
FIG. 41 is a close-up of the insertion sleeve retracted.

FIG. 41 is a close-up view of a delivery tip of the device 3901 with the insertion sleeve 3951 retracted. As shown, a distal portion of the shaft 3903 is exposed and the slit 3651 and the open cutaways 3567 have allowed the insertion sleeve 3951 to open. The delivery tool has at least one blade 3909 and may include a pair of blades 3908, 3909 that extend from a rod that extends from the handle 3905 and through the shaft 3903 of the device 3901. A bone anchor 4401 is carried between the two blades 3908, 3909. Embodiments of the invention use only one blade 3909 and the choice between one or two blades involves a modest tradeoff between ease of delivery through porous or thin-shelled bone (single blade 3909 may be better) or extra rigidity for dense bone (two blade may be preferred). The depicted bone anchor 4401 is discussed in more detail below. Preferably, a distal end of the shaft 3903 has a bridge 4117 (e.g., a tab or overhang) that sits behind a base of the anchor 4401.

Figure 42:
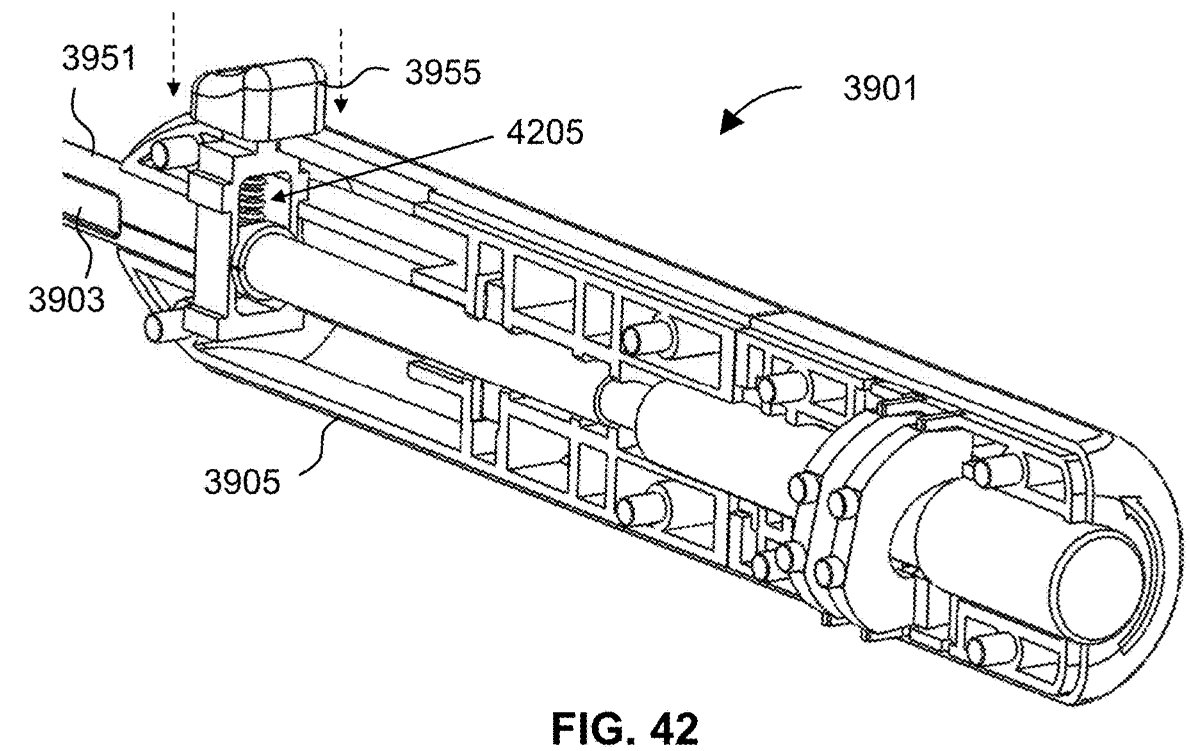
FIG. 42 is a cutaway view of the slider knob delivery tool.

FIG. 42 is a cutaway view of the bone anchor delivery tool 3901 with an insertion sleeve 3951 covering the shaft 3903 that extends from the handle 3905 with the slider knob 3955 being depressed. A spring 4205 keeps the slider knob 3955 within a notch or détente that prevents any motion along a proximal/distal axis when the knob 3955 is not pressed, as shown.

Figure 43:
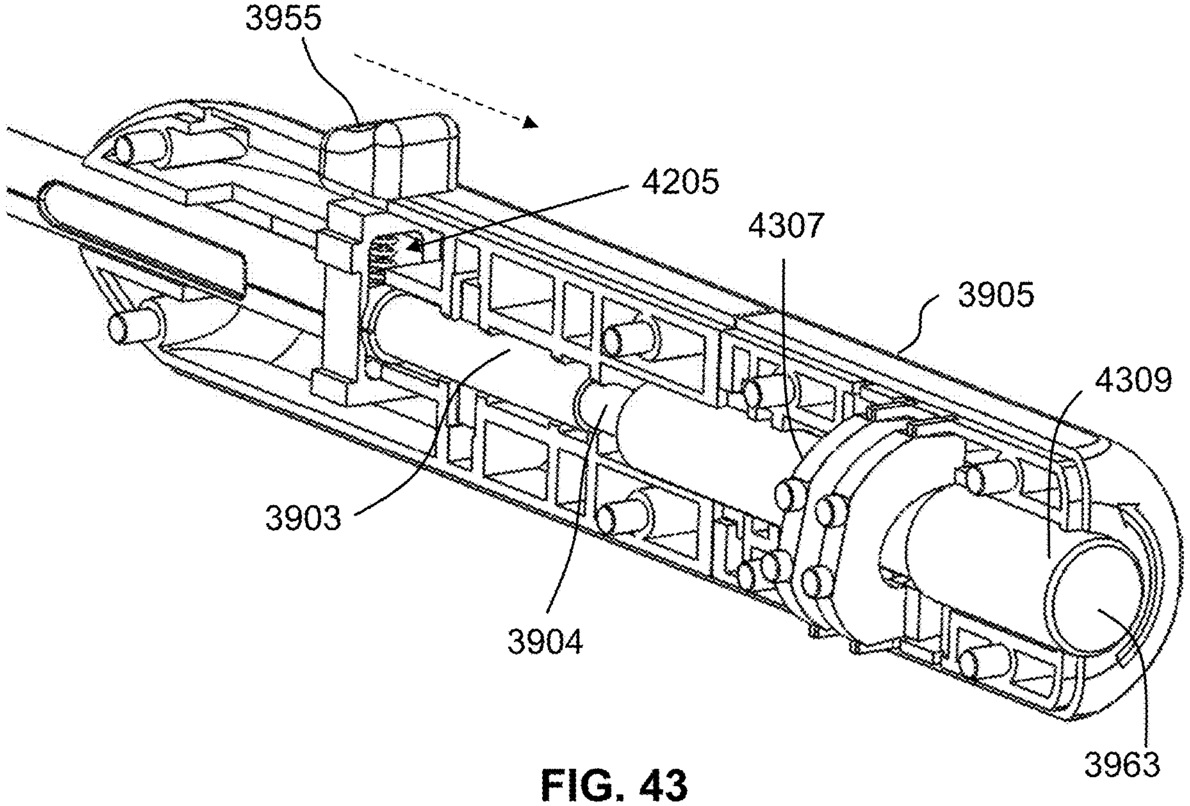
FIG. 43 shows the slider knob being pulled back to retract the sleeve.

FIG. 43 shows the slider knob 3955 being pressed, the spring 4205, and the slider knob 3955 being slid in a proximal direction, retracting the sleeve 3951 to expose the delivery tip as shown in FIG. 41. As shown, the shaft 3903 includes a slidable rod 3904 extending therethrough operable to translate the first blade 3909. Preferably, a proximal end of the handle 3905 presents a flat or solid head surface 3963. When the sharpened tapered tip of the blade 3909 is positioned against bone and the flat or solid head surface 3963 is hammered with a mallet, the sharpened tapered tip pierces a hole in the bone and the delivery tool 3901 carries the bone anchor 4401 into the bone down to the base.

In the depicted embodiment, a distal portion of the shaft 3903 is covered by the insertion sleeve 3951. The insertion sleeve 3951 may be a plastic or elastic material with a tapered tip and may include a split 3561 into the tapered tip, so that the tapered tip defines two semi-conical portions that allow the distal tip to bend open when the sleeve is retracted over the shaft 3903. The insertion sleeve 3951 may provide important safety and utility benefits by protecting handlers from the sharped blades 3908, 3909 and also keeping the anchor 4401 in place from unpackaging up until delivery.

A surgeon can navigate the shaft through a surgical incision or cannula and position the anchor at a target sit over bone (and over a graft positioned on the bone). The surgeon can drive the blades (and the carried anchor) into the bone, which may be accomplished by tapping the surface 3963 at the base of the handle with a mallet. The handle also includes a mechanism to retract the blades into the handle. The mechanism preferably include a threaded fitting 4307 around the rod 3904 wherein a knob 4309 exposed at the handle can be turned to withdraw the blades into the handle via a screw-drive provided by the threaded fitting 4307. As shown, the knob 4309 and the surface 3963 are of the same piece, but they may also be provided as separate parts, e.g., a surface 3963 presented coaxially within the knob such that rotating the knob does not rotate the surface 3963. A distal end of the shaft 3903 has a bridge 4117 (e.g., a tab or overhang) that sits behind a base of the anchor 4401. As the surgeon screws the knob 4309, the bridge 4117 may keep the anchor 4401 sitting in the bone while the blades 3908, 3909 are withdrawn slowly and gently into the shaft 3903 (leaving only the anchor 4401 in the bone).

Figure 44:
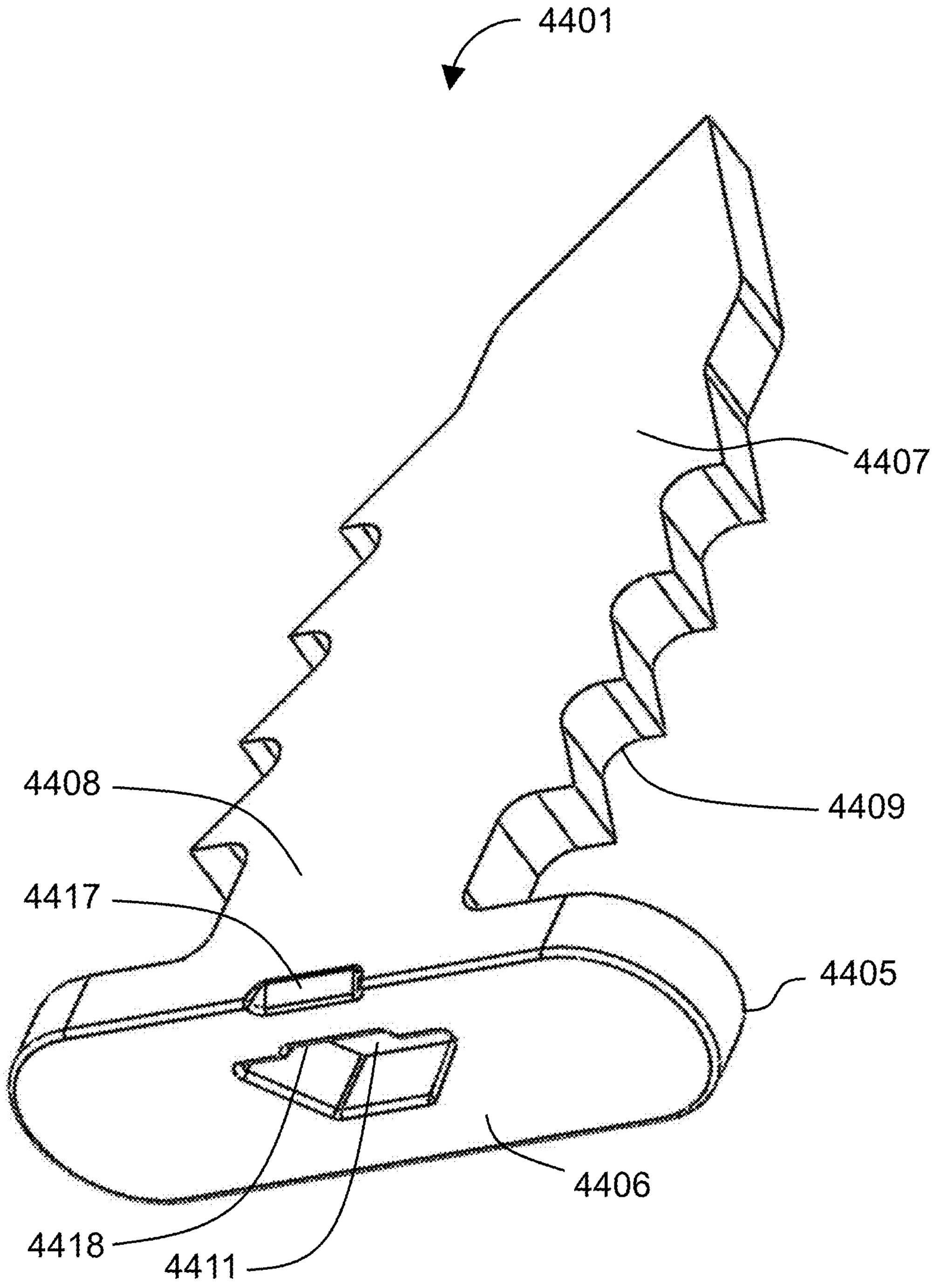
FIG. 44 shows a bone anchor with ramps and blade-shaped opening.

FIG. 44 shows a bone anchor 4401. The bone anchor includes a base 4405, a stake 4407 extending substantially perpendicular from the base 4405, and an open portion 4411 in the base through which the first blade 3909 may extend. In some embodiments, the open portion 4411 defines a substantially trapezoidal hole through the base 4405, wherein a long side of the hole cooperates with the first substantially planar surface of the stake to define an essentially flat surface against which the first blade lies. The bone anchor may be made from an absorbable polymer (e.g. PEEK, POM, Nylon, HDPE), bioabsorbable polymer (e.g. PLA, PGA, PDS, PLGA), or a biological metrical such as collagen or bone.

A bone anchor 4401 of the disclosure may include a sloped face 4417, creating an intermediate transition between a pushable, proximal face 4406 of the base 4405 and a first extended flat face 4408 of the stake 4407. When the bone anchor 4401 is loaded on the delivery tool 3901, the first extended flat face 4408 lies against a flat side of the blade 3908.

The bone anchor 4401, as shown, has a second sloped face 4418 along a perimeter of the open portion 4411 through the base 4405. The stake 4407 has a second extended flat surface 4409, obverse to the first extended flat face 4408. When the bone anchor 4401 is loaded on the delivery tool 3901, the second extended flat face 4409 lies against a flat side of the blade 3909.

The sloped faces 4417, 4418 facilitate easier insertion of the blade(s) 3908, 3909 into the fastener 4401, e.g., during device assembly or during reloading. By having the sloped faces 4417, 4418 present, a user loading the bone anchor 4401 need only have the manual dexterity and precision to position the sharpened tips of the blades 3908, 3909 within the cutaway spaces defined by the sloped faces 4417, 4418. Then, sliding the bone anchor 4401 onto the blades 3908, 3909, the beveled edges of the sloped faces 4417, 4418 and the sloped faces 4417, 4418 themselves guide the bone anchor 4401 into the proper orientation.

Additionally, as shown, the bone anchor 4401 has an open portion 4411 through the base 4405 through which the first blade 3909 may extend. The shape of the open portion 4411 correlates to the shape of the cross section of the blade 3909, facilitating a tight fit between the blade 3909 and the bone anchor 4401 therefore preventing unwanted lateral rotation of the bone anchor 4401 in relation to the blade 3909 or any other movement of the bone anchor 4401 prior to insertion into bone.

Bone anchor embodiments shown herein exhibit a common feature in that a tool carries a bone anchor and pierces, through a graft or ligament or tissue, and into bone, making a hole, while carrying the bone anchor into the hole and leaving the bone anchor in the hole when the delivery tool is retracted. These embodiments offer something new for arthroscopic and orthopedic surgery that has previously required some version of creating a pilot hole and/or drilling bone with a first tool and then removing the first tool and brining a separate second tool to deliver an anchor into the hole. For example, simply using bone as an example, some prior approaches require a first tool to make a pilot hole into bone. After the spike or drill that makes that pilot hole is pulled back, then an anchor or other fastener is inserted into the pilot hole. Those approaches were suboptimal in keyhole surgery because small disturbances to the site could lose alignment, making it very difficult to place the bone anchor in the pilot hole. With devices, methods, and systems shown herein, a delivery tool simultaneously cuts open the bone, making the hole, while bringing the implantable anchor into the hole.

The invention claimed is:

1. A bone anchor delivery system, the system comprising:

a delivery tool comprising
- a handle,
- an elongated shaft extending from the handle,
- a slidable rod extending through the shaft,
- a first blade extending distally from the slidable rod to a sharpened bone-piercing tip, wherein the slidable rod is operable to translate the first blade between a first, distal position, wherein the first blade extends distally from the shaft, and a second, proximal position in which the first blade is retracted proximally into the shaft; and an implantable bone anchor disposed upon the first blade, the bone anchor comprising
- a base,
- a flat stake extending perpendicular from the base, the stake comprising opposed first and second planar surfaces that meet at first and second barbed or serrated edges, and a distal point, and
- an open portion defining a slot through the base through which the first blade extends, wherein a flat side of the slot cooperates with the first planar surface of the stake to define a flat surface against which the first blade lies.

2. The system of claim 1, wherein the delivery tool comprises a second blade, wherein the first blade and the second blade sit against the opposed first and second planar surfaces of the stake of the bone anchor.

3. The system of claim 2, wherein the first and second blades comprise a rigid metal, wherein the bone anchor comprises a pliable material, and wherein the first and second blades prevent the bone anchor from deforming during delivery.

4. The system of claim 2, wherein the bone anchor includes at least two lateral barbs that protrude in opposed lateral directions, and wherein the first and second blades puncture or cut into bone in the opposed lateral directions, and/or where the barbs and the blades are not co-planar.

5. The system of claim 1, wherein the stake of the bone anchor has a plurality of teeth along first and second edges.

6. The system of claim 1, wherein the bone anchor is made from an absorbable polymer.

7. The system of claim 1, wherein the base of the bone anchor comprises overhangs that extend away from the stake in multiple directions.

8. The system of claim 1, further comprising an insertion sleeve disposed slidably over the shaft, wherein a distal end of the insertion sleeve can be opened by sliding the insertion sleeve in a proximal direction over the shaft.

9. The system of claim 8, wherein the insertion sleeve comprises an elastic deformable material and a slit separating two portions of a distal tip, wherein the insertion sleeve opens by bending the two portions of the distal tip elastically away from one another.

10. The system of claim 8, wherein retracting the insertion sleeve exposes the bone anchor and/or blade in a distal direction out of the protection sleeve.

11. The system of claim 1, wherein the bone anchor comprises at least one sloped face providing a transition between the first planar surface of the stake and a proximal-most face of the base.

12. The system of claim 11, wherein the sloped face—when a sharpened tip of the first blade is positioned within a cutaway space defined by the sloped face—guides the bone anchor into position while the bone anchor is being loaded onto the delivery tool.

13. A bone anchor delivery system, the system comprising:

a delivery tool comprising
- a handle, an elongated shaft extending from the handle, a first blade and a second blade each extending distally from a rod extending through the shaft to respective first and second sharpened bone-piercing tips, and a knob on the handle attached to the rod via a threaded fitting, wherein twisting the knob translates the rod with respect to the shaft; and an implantable bone anchor disposed upon the first blade, the bone anchor comprising a base, a stake extending perpendicular from the base, wherein the first and second blade sit against respective opposed surfaces of the stake of the bone anchor, and an open portion in the base through which the first blade extends.

14. The system of claim 13, wherein when the first blade and the second blade are in distal positions with the stake of the bone anchor therebetween, first blade, the second blade, and the stake cooperate to present a sharpened tapered tip useful to pierce into bone.

15. The system of claim 14, wherein a proximal end of the knob presents a flat head surface.

16. The system of claim 15, wherein when the sharpened tapered tip is positioned against bone and the flat head surface is hammered with a mallet, the sharpened tapered tip pierces a hole in the bone and the delivery tool carries the bone anchor into the bone down to the base.

17. The system of claim 13, further comprising an extraction bridge spanning across the distal end of the shaft and adapted to hold the implantable bone anchor in place while the first and second blades are retracted.

18. A method of anchoring a graft to bone, the method comprising:

using a system of claim 13 to carry the bone anchor disposed on the blade through an incision to a target site on bone;

driving the anchor and the blade into the bone;

retracting the rod in a proximal direction into the shaft to remove the blade from the bone anchor while the bone anchor is sitting in the bone, wherein the retracting step includes screwing the knob on the handle to draw the blade into the handle without any kinetic shocks or reciprocal motions on the delivery tool; and removing the delivery tool from the target site and out of the incision.

19. A bone anchor delivery system, the system comprising:

a delivery tool comprising a handle, an elongated shaft extending from the handle, a first blade extending distally from a rod extending through the shaft to a sharpened bone-piercing tip, an insertion sleeve disposed slidably over the shaft, wherein a distal end of the insertion sleeve can be opened by sliding the insertion sleeve in a proximal direction over the elongated shaft, and a slider knob on the handle, wherein pushing the slider knob and sliding the slider knob in a proximal direction slides the insertion sleeve in the proximal direction over the elongated shaft; and an implantable bone anchor disposed upon the first blade, the bone anchor comprising a base, a stake extending perpendicular from the base, and an open portion in the base through which the first blade extends.

* * * * *